US012616528B2

(12) United States Patent
Row et al.

(10) Patent No.: US 12,616,528 B2
(45) Date of Patent: May 5, 2026

(54) METHODS AND SYSTEMS FOR PERFORMING COMPUTER ASSISTED SURGERY

(71) Applicant: Mobius Imaging, LLC, Shirley, MA (US)

(72) Inventors: Gordon Row, Groton, MA (US); Kyle Schwartz, Somerville, MA (US); Edward Daley, Maynard, MA (US); Scott Coppen, Amesbury, MA (US); Todd Furlong, Goffstown, NH (US); Michael Everman, Goleta, CA (US)

(73) Assignee: Mobius Imaging, LLC, Shirley, MA (US)

( * ) Notice: Subject to any disclaimer, the term of this patent is extended or adjusted under 35 U.S.C. 154(b) by 0 days.

(21) Appl. No.: 18/594,379

(22) Filed: Mar. 4, 2024

(65) Prior Publication Data

US 2024/0245469 A1 Jul. 25, 2024

Related U.S. Application Data

(63) Continuation of application No. 18/142,817, filed on May 3, 2023, now Pat. No. 11,950,858, which is a (Continued)

(51) Int. Cl.
*A61B 34/20* (2016.01)
*A61B 34/30* (2016.01)
*A61B 90/00* (2016.01)

(52) U.S. Cl.
CPC .............. *A61B 34/20* (2016.02); *A61B 34/30* (2016.02); *A61B 90/39* (2016.02);

(Continued)

(58) Field of Classification Search
CPC .... A61B 2090/3945; A61B 2090/3937; A61B 90/39; A61B 2090/3983; A61B 34/20;

(Continued)

(56) References Cited

U.S. PATENT DOCUMENTS

| 5,375,480 A | 12/1994 | Nihei et al. |
| 5,799,055 A | 8/1998 | Peshkin et al. |

(Continued)

FOREIGN PATENT DOCUMENTS

| CA | 2957977 A1 | 4/2017 |
| CN | 201422918 Y | 3/2010 |

(Continued)

OTHER PUBLICATIONS

English language abstract and machine-assisted English translation for CN 101579269 extracted from espacenet.com database on Jan. 9, 2020, 8 pages.

(Continued)

*Primary Examiner* — Chao Sheng

(74) *Attorney, Agent, or Firm* — Howard & Howard Attorneys PLLC

(57) ABSTRACT

Methods and systems for performing computer-assisted surgery, including robot-assisted image-guided surgery. Embodiments include marker devices for an image guided surgery system, marker systems and arrays for tracking a robotic arm using a motion tracking system, and image guided surgery methods and systems using optical sensors.

17 Claims, 21 Drawing Sheets

Related U.S. Application Data continuation of application No. 16/605,759, filed as application No. PCT/US2018/054699 on Oct. 5, 2018, now Pat. No. 11,678,939.

(60) Provisional application No. 62/568,354, filed on Oct. 5, 2017.

(52) U.S. Cl.
CPC .................. *A61B 2034/2048* (2016.02); *A61B 2034/2055* (2016.02); *A61B 2034/2072* (2016.02); *A61B 2034/306* (2016.02); *A61B 2090/3945* (2016.02); *A61B 2090/3983* (2016.02)

(58) Field of Classification Search
CPC ............ A61B 34/30; A61B 2034/2048; A61B 2034/2055; A61B 2034/2072; A61B 2034/306
See application file for complete search history.

(56) References Cited

U.S. PATENT DOCUMENTS

| | | | |
|---|---|---|---|
| 5,921,992 | A | 7/1999 | Costales et al. |
| 6,149,592 | A | 11/2000 | Yanof et al. |
| 6,236,875 | B1 | 5/2001 | Bucholz et al. |
| 6,275,725 | B1 | 8/2001 | Cosman |
| 6,533,455 | B2 | 3/2003 | Graumann et al. |
| 6,685,698 | B2 | 2/2004 | Morley et al. |
| 6,772,002 | B2 | 8/2004 | Schmidt et al. |
| 6,785,572 | B2 | 8/2004 | Yanof et al. |
| 7,194,120 | B2 | 3/2007 | Wicker et al. |
| 7,251,522 | B2 | 7/2007 | Essenreiter et al. |
| 7,587,235 | B2 | 9/2009 | Wist et al. |
| 7,699,877 | B2 | 4/2010 | Davison |
| 7,722,530 | B2 | 5/2010 | Davison |
| 7,799,036 | B2 | 9/2010 | Davison et al. |
| 8,016,835 | B2 | 9/2011 | Birkmeyer et al. |
| 8,046,054 | B2 | 10/2011 | Kim et al. |
| 8,118,488 | B2 | 2/2012 | Gregerson |
| 8,126,114 | B2 | 2/2012 | Naylor et al. |
| 8,394,144 | B2 | 3/2013 | Zehavi et al. |
| 8,454,583 | B2 | 6/2013 | Perez-Cruet et al. |
| 8,457,790 | B2 | 6/2013 | Blondel et al. |
| 8,509,503 | B2 | 8/2013 | Nahum et al. |
| 8,761,337 | B2 | 6/2014 | Naylor et al. |
| 8,795,188 | B2 | 8/2014 | Maschke |
| 8,974,460 | B2 | 3/2015 | De la Fuente Klein et al. |
| 9,125,680 | B2 | 9/2015 | Kostrzewski et al. |
| 9,237,861 | B2 | 1/2016 | Nahum et al. |
| 9,259,282 | B2 | 2/2016 | Azizian et al. |
| 9,283,048 | B2 | 3/2016 | Kostrzewski et al. |
| 9,308,050 | B2 | 4/2016 | Kostrzewski et al. |
| 9,545,233 | B2 | 1/2017 | Sirpad et al. |
| 9,550,299 | B2 | 1/2017 | Wolf et al. |
| 9,750,432 | B2 | 9/2017 | Nahum et al. |
| 9,833,292 | B2 | 12/2017 | Kostrzewski et al. |
| 10,004,562 | B2 | 6/2018 | Kostrzewski et al. |
| 10,039,476 | B2 | 8/2018 | Nahum et al. |
| 10,064,682 | B2 | 9/2018 | Azizian et al. |
| 10,076,385 | B2 | 9/2018 | Shoham et al. |
| 10,136,952 | B2 | 11/2018 | Couture et al. |
| 10,159,534 | B2 | 12/2018 | Maillet et al. |
| 10,772,577 | B2 | 9/2020 | Fortuna et al. |
| 11,678,939 | B2 | 6/2023 | Row et al. |
| 2003/0012342 | A1 | 1/2003 | Suhm et al. |
| 2006/0082546 | A1* | 4/2006 | Wey ..................... G06F 3/0325 |
| | | | 345/156 |
| 2006/0082789 | A1 | 4/2006 | Goldbach |
| 2006/0262315 | A1 | 11/2006 | Spanner |
| 2007/0081695 | A1 | 4/2007 | Foxlin et al. |
| 2007/0156157 | A1 | 7/2007 | Nahum et al. |
| 2008/0306490 | A1 | 12/2008 | Lakin et al. |

| | | | |
|---|---|---|---|
| 2009/0088772 | A1 | 4/2009 | Blumenkranz |
| 2010/0274389 | A1 | 10/2010 | Ortmaier et al. |
| 2011/0105895 | A1 | 5/2011 | Kornblau et al. |
| 2012/0184839 | A1 | 7/2012 | Woerlein |
| 2013/0041509 | A1 | 2/2013 | Saito et al. |
| 2014/0003572 | A1 | 1/2014 | Gregerson et al. |
| 2014/0139215 | A1 | 5/2014 | Gregerson et al. |
| 2014/0249546 | A1 | 9/2014 | Shvartsberg et al. |
| 2014/0265182 | A1 | 9/2014 | Stanton et al. |
| 2014/0267773 | A1* | 9/2014 | Jeung ........................ F21V 9/08 |
| | | | 362/555 |
| 2014/0275953 | A1 | 9/2014 | Gregerson et al. |
| 2015/0202009 | A1 | 7/2015 | Nussbaumer et al. |
| 2015/0366624 | A1 | 12/2015 | Kostrzewski et al. |
| 2016/0030117 | A1 | 2/2016 | Mewes |
| 2016/0081754 | A1 | 3/2016 | Kostrzewski et al. |
| 2016/0174914 | A1 | 6/2016 | Lerch et al. |
| 2016/0220320 | A1 | 8/2016 | Crawford et al. |
| 2016/0235492 | A1 | 8/2016 | Morard et al. |
| 2016/0278875 | A1 | 9/2016 | Crawford et al. |
| 2016/0302871 | A1 | 10/2016 | Gregerson et al. |
| 2016/0360954 | A1 | 12/2016 | Rohling et al. |
| 2017/0071691 | A1 | 3/2017 | Crawford et al. |
| 2017/0079727 | A1 | 3/2017 | Crawford et al. |
| 2017/0086941 | A1 | 3/2017 | Marti et al. |
| 2017/0172669 | A1 | 6/2017 | Berkowitz et al. |
| 2017/0202452 | A1* | 7/2017 | Li ........................ A61B 5/0066 |
| 2017/0231702 | A1 | 8/2017 | Crawford et al. |
| 2017/0239002 | A1 | 8/2017 | Crawford et al. |
| 2017/0239003 | A1 | 8/2017 | Crawford et al. |
| 2017/0239006 | A1 | 8/2017 | Crawford et al. |
| 2017/0245951 | A1 | 8/2017 | Crawford et al. |
| 2017/0252112 | A1 | 9/2017 | Crawford et al. |
| 2017/0258533 | A1 | 9/2017 | Crawford et al. |
| 2017/0258535 | A1 | 9/2017 | Crawford et al. |
| 2017/0312035 | A1* | 11/2017 | May ..................... A61B 50/33 |
| 2017/0312039 | A1 | 11/2017 | Crawford et al. |
| 2017/0348061 | A1 | 12/2017 | Joshi et al. |
| 2017/0360513 | A1 | 12/2017 | Amiot et al. |
| 2017/0360517 | A1 | 12/2017 | Crawford et al. |
| 2018/0000546 | A1 | 1/2018 | Crawford et al. |
| 2018/0014888 | A1 | 1/2018 | Bonny et al. |
| 2018/0110573 | A1 | 4/2018 | Kostrzewski |
| 2018/0116739 | A1 | 5/2018 | Gogarty et al. |
| 2018/0116740 | A1 | 5/2018 | Gogarty et al. |
| 2018/0125597 | A1 | 5/2018 | Gogarty et al. |
| 2018/0157238 | A1 | 6/2018 | Gogarty et al. |
| 2018/0207794 | A1 | 7/2018 | Sebring et al. |
| 2018/0221098 | A1 | 8/2018 | Forsyth et al. |
| 2018/0235715 | A1 | 8/2018 | Amiot et al. |
| 2018/0250077 | A1 | 9/2018 | Xu et al. |
| 2018/0256259 | A1 | 9/2018 | Crawford |
| 2018/0271605 | A1 | 9/2018 | Kostrzewski et al. |
| 2018/0346008 | A1 | 12/2018 | Nahum et al. |
| 2019/0000561 | A1 | 1/2019 | Decker et al. |
| 2019/0000569 | A1 | 1/2019 | Crawford et al. |
| 2019/0021795 | A1 | 1/2019 | Crawford et al. |
| 2019/0021799 | A1 | 1/2019 | Crawford et al. |
| 2019/0021800 | A1 | 1/2019 | Crawford et al. |
| 2019/0029759 | A1 | 1/2019 | Mcdonell |
| 2019/0029765 | A1 | 1/2019 | Crawford et al. |
| 2019/0038362 | A1 | 2/2019 | Nash et al. |
| 2019/0053859 | A1 | 2/2019 | Couture et al. |
| 2019/0069961 | A1 | 3/2019 | Smith et al. |
| 2019/0099222 | A1 | 4/2019 | Nahum et al. |
| 2019/0117313 | A1 | 4/2019 | Crawford |
| 2019/0142533 | A1 | 5/2019 | Itkowitz et al. |
| 2019/0239964 | A1 | 8/2019 | LeBoeuf, II et al. |
| 2019/0269467 | A1 | 9/2019 | Forsyth et al. |
| 2019/0274765 | A1 | 9/2019 | Crawford et al. |
| 2020/0146754 | A1 | 5/2020 | Row et al. |
| 2023/0263579 | A1 | 8/2023 | Row et al. |

FOREIGN PATENT DOCUMENTS

| | | | |
|---|---|---|---|
| CN | 201542641 | U | 8/2010 |
| CN | 101700184 | B | 1/2011 |
| CN | 101579269 | B | 4/2011 |
| CN | 101853333 | B | 11/2012 |

(56) References Cited

FOREIGN PATENT DOCUMENTS

| | | | |
|---|---|---|---|
| WO | 2015115809 | A1 | 8/2015 |
| WO | 2016096675 | A1 | 6/2016 |
| WO | 2016141378 | A1 | 9/2016 |
| WO | 2017036340 | A1 | 3/2017 |
| WO | 2017122202 | A1 | 7/2017 |
| WO | 2018185729 | A1 | 10/2018 |

OTHER PUBLICATIONS

English language abstract and machine-assisted English translation for CN 101700184 extracted from espacenet.com database on Jan. 9, 2020, 10 pages.

English language abstract and machine-assisted English translation for CN 101853333 extracted from espacenet.com database on Jan. 9, 2020, 9 pages.

English language abstract and machine-assisted English translation for CN 201422918 extracted from espacenet.com database on Jan. 9, 2020, 7 pages.

English language abstract and machine-assisted English translation for CN 201542641 extracted from espacenet.com database on Jan. 9, 2020, 10 pages.

English language abstract and machine-assisted English translation for WO 2015/115809 extracted from espacenet.com database on Jan. 9, 2020, 8 pages.

English language abstract for WO 2017/036340 extracted from espacenet.com database on Jan. 9, 2020, 2 pages.

International Search Report received from the Korean Intellectual Property Office in related Application No. PCT/US2018/054699 dated Jul. 12, 2019.

PAL jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

Written Opinion received from the Korean Intellectual Property Office in related Application No. PCT/US2018/054699 dated Jul. 12, 2019.

* cited by examiner

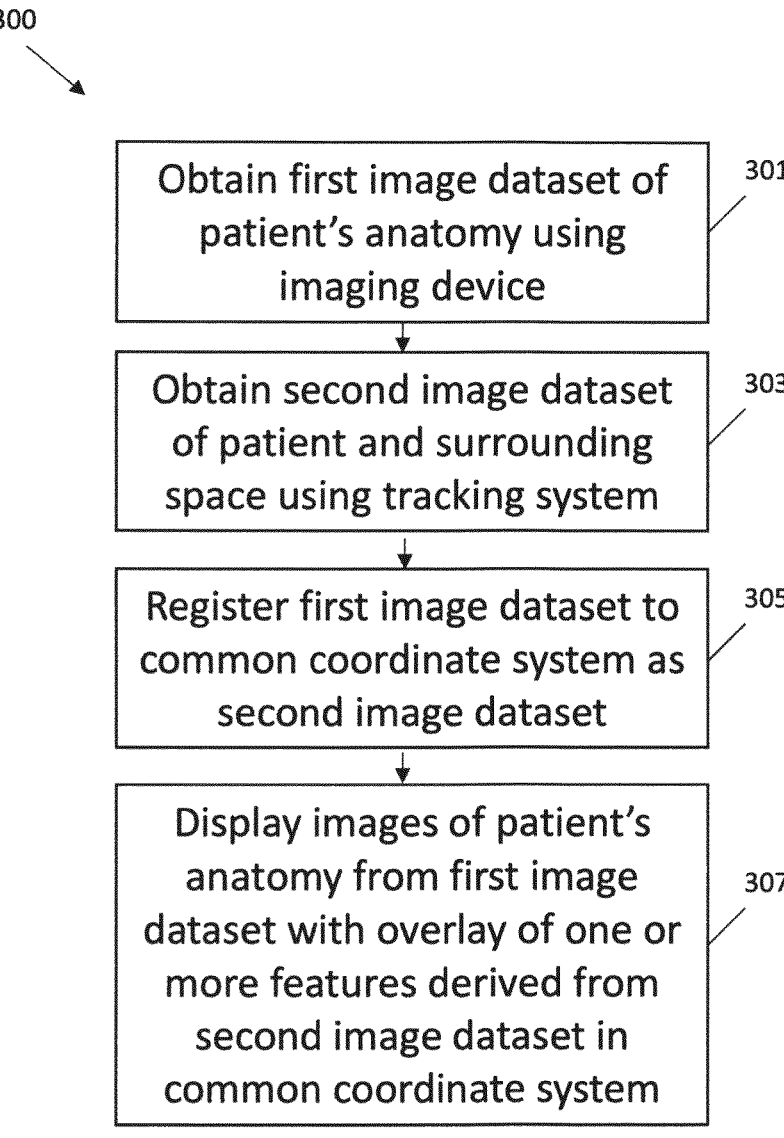

300

Obtain first image dataset of patient's anatomy using imaging device — 301

Obtain second image dataset of patient and surrounding space using tracking system — 303

Register first image dataset to common coordinate system as second image dataset — 305

Display images of patient's anatomy from first image dataset with overlay of one or more features derived from second image dataset in common coordinate system — 307

FIG. 3

METHODS AND SYSTEMS FOR PERFORMING COMPUTER ASSISTED SURGERY

RELATED APPLICATIONS

This application is a Continuation of U.S. patent application Ser. No. 18/142,817 filed on May 3, 2023, which is a Continuation of U.S. patent application Ser. No. 16/605, 759 filed on Oct. 16, 2019, issued as U.S. Pat. No. 11,678, 939, which is the U.S. National Stage Entry of International Patent Application No. PCT/US2018/054699 filed on Oct. 5, 2018, which claims the benefit of priority to U.S. Provisional Patent Application No. 62/568,354 filed on Oct. 5, 2017, the disclosures of which are hereby incorporated by reference in their entirety.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained using pre-operative or intra-operative medical imaging (e.g., x-ray computed tomography (CT) or magnetic resonance (MR) imaging), to the actual position of the patient and/or other objects (e.g., surgical instruments, robotic manipulator(s) or end effector(s) in the surgical area. These procedures may be used to aid the surgeon in planning a surgical procedure and may also provide the surgeon with relevant feedback during the course of surgical procedure. There is a continuing need to improve the safety and ease-of-use of computer-assisted surgical systems.

SUMMARY

Various embodiments include methods and systems for performing computer-assisted surgery, including robot-assisted image-guided surgery.

Embodiments include a marker device for an image guided surgery system that includes an electronics unit having at least one light source, a rigid frame attached to the electronics unit, the rigid frame having at least one channel extending from the electronics unit to at least one opening in the rigid frame, and an optical guide apparatus located within the at least one channel to couple light from the at least one light source of the electronics unit to the at least one opening in the rigid frame.

Further embodiments include a marker device for an image guided surgery system that includes an electronics unit including a flexible circuit having a plurality of peripheral arm regions and a light source located on each of the peripheral arm regions, and a rigid frame attached to the electronics unit, the rigid frame having a plurality of channels terminating in openings in the rigid frame, each of the plurality of peripheral arm regions located within a channel with each of the plurality of light sources configured to direct light from a respective opening in the rigid frame.

Further embodiments include a marker system for tracking a robotic arm using a motion tracking system that includes a light source located within the robotic arm, and a marker comprising an optical diffuser that attaches to an outer surface of the robotic arm to optically couple the light source to the diffuser.

Further embodiments include a marker array having a plurality of markers for tracking a robotic arm that includes multiple axes between a proximal end and a distal end of the robotic arm, and an end effector attached to the distal end of the robotic arm, where the marker array includes at least one first marker that is distal to the most distal axis of the robotic arm, and at least one second marker that is proximal to the most distal axis of the robotic arm.

Further embodiments include a multi-axis robotic arm that includes a first section that comprises at least one axis that provides both pitch and yaw rotation, a second section, distal to the first section, that comprises two mutually orthogonal rotary wrist axes, and an end effector coupled to the second section.

Further embodiments include an image guided surgery system that includes an optical sensor facing in a first direction to detect optical signals from a marker device located in a surgical site, a reference marker device located along a second direction with respect to the optical sensor, and a beam splitter optically coupled to the optical sensor and configured to redirect optical signals from the reference marker device to the optical sensor.

Further embodiments include an optical sensing device for a motion tracking system that includes a support structure, at least one optical sensor mounted to the support structure and configured to generate tracking data of one or more objects within a field-of-view of the optical sensor, and an inertial measurement unit mounted to the support structure and configured to detect a movement of the at least one optical sensor.

Further embodiments include an image guided surgery system that includes a marker device, a least one optical sensor configured to detect optical signals from the marker device, an inertial measurement unit mechanically coupled to the at least one optical sensor and configured to measure a movement of the at least one optical sensor, and a processing system, coupled to the at least one optical sensor and the inertial measurement unit, and including at least one processor configured with processor-executable instructions to perform operations including tracking the position and orientation of the marker device based on the optical signals received at the at least one optical sensor, receiving measurement data from the inertial measurement unit indicating a movement of the at least one optical sensor, and correcting the tracked position and orientation of the marker device based on the measurement data from the inertial measurement unit.

Further embodiments include a method of performing image guided surgery that includes tracking the position and orientation of a marker device based on optical signals from the marker device received by at least one optical sensor, receiving measurement data from an inertial measurement unit indicating a movement of the at least one optical sensor, and correcting the tracked position and orientation of the marker device based on the measurement data from the inertial measurement unit.

Further embodiments include an image guided robotic surgery system that includes a robotic arm, a plurality of marker devices, a sensor array located on the robotic arm and configured to detect optical signals from the plurality of marker devices, and a processing system, coupled to the sensor array, and configured to track the position of the plurality of marker devices in three-dimensional space based on the detected optical signals from the sensor array and the joint coordinates of the robotic arm.

BRIEF DESCRIPTION OF THE DRAWINGS

Other features and advantages of the present invention will be apparent from the following detailed description of the invention, taken in conjunction with the accompanying drawings of which:

FIG. 3 is a process flow diagram illustrating a method for performing registration of patient image data for image-guided surgery.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
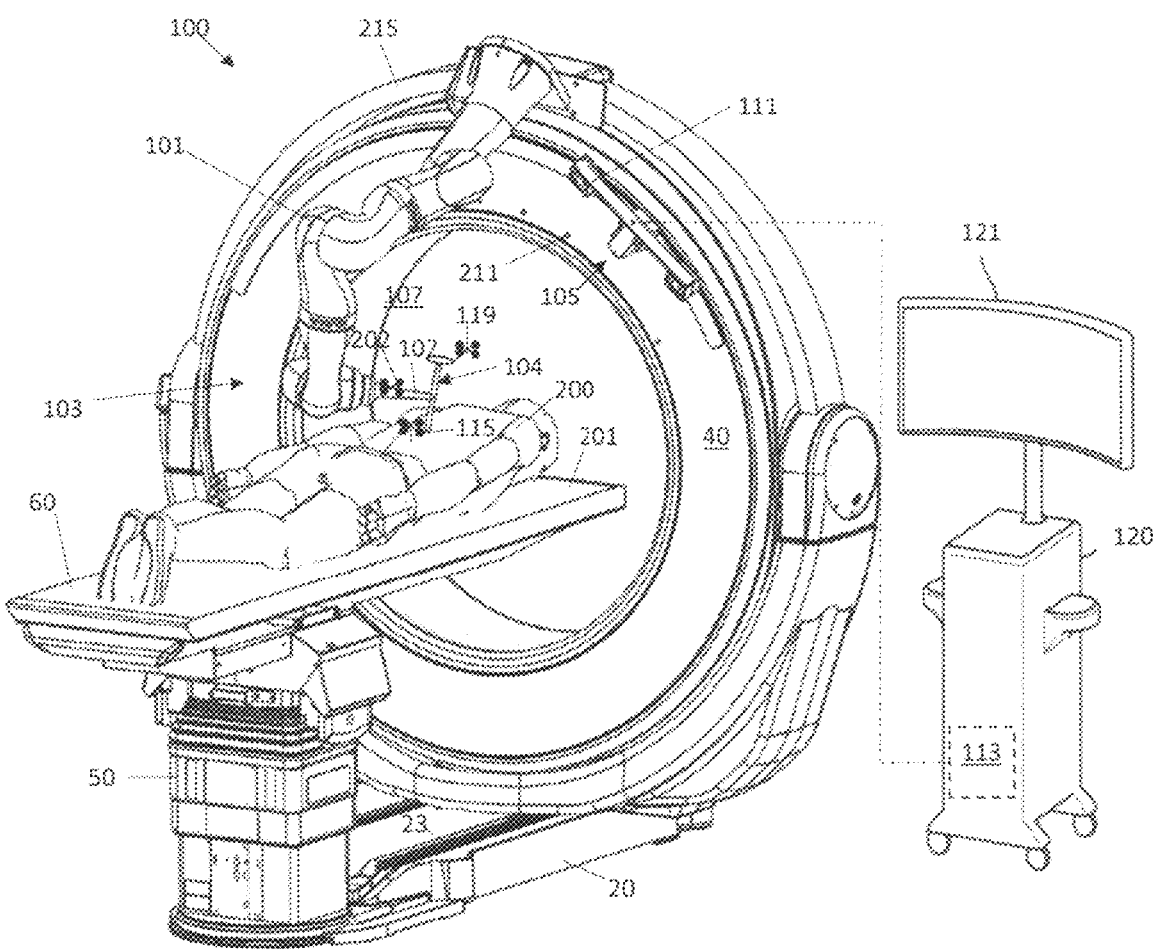
FIG. 1 is a perspective view of a system for performing robotically-assisted image-guided surgery according to an embodiment.

FIG. 1 illustrates a system 100 for performing computer assisted surgery, including robotically-assisted image-guided surgery according to various embodiments. The system 100 in this embodiment includes an imaging device 103, a motion tracking system 105 and a robotic arm 101 for performing a robotically-assisted surgical procedure. The robotic arm 101 may comprise a multi-joint arm that includes a plurality of linkages connected by joints having actuator(s) and optional encoder(s) to enable the linkages to rotate, bend and/or translate relative to one another in response to control signals from a robot control system. The robotic arm 101 may be fixed to a support structure at one end and may have an end effector 102 at the other end of the robotic arm 101.

The imaging device 103 may be used to obtain diagnostic images of a patient 200, which may be a human or animal patient. In embodiments, the imaging device 103 may be an x-ray computed tomography (CT) imaging device. The patient 200 may be positioned within a central bore 107 of the imaging device 103 and an x-ray source and detector may be rotated around the bore 107 to obtain x-ray image data (e.g., raw x-ray projection data) of the patient 200. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure) or intra-operatively (i.e., during a surgical procedure) by positioning the patient 200 within the bore 107 of the imaging device 103. In the system 100 of FIG. 1, this may be accomplished by moving the imaging device 103 over the patient 200 to perform a scan while the patient 200 may remain stationary.

Examples of x-ray CT imaging devices that may be used according to various embodiments are described in, for example, U.S. Pat. No. 8,118,488, U.S. patent Application Publication No. 2014/0139215, U.S. patent Application Publication No. 2014/0003572, U.S. Patent Application Publication No. 2014/0265182 and U.S. patent Application Publication No. 2014/0275953, the entire contents of all of which are incorporated herein by reference. In the embodiment shown in FIG. 1, the patient support 60 (e.g., surgical table) upon which the patient 200 may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient 200, and may translate away from the patient 200 to an out-of-the-way position for performing a surgical procedure on the patient 200.

An example imaging device 103 that may be used in various embodiments is the AIRO® intra-operative CT system manufactured by Mobius Imaging, LLC and distributed by Brainlab, AG. Other imaging devices may also be utilized. For example, the imaging device 103 may be a mobile CT device that is not attached to the patient support 60 and may be wheeled or otherwise moved over the patient 200 and the support 60 to perform a scan. Examples of mobile CT devices include the BodyTom® CT scanner from Samsung Electronics Co., Ltd. and the O-arm® surgical imaging system form Medtronic, plc. The imaging device 103 may also be a C-arm x-ray fluoroscopy device. In other embodiments, the imaging device 103 may be a fixed-bore imaging device, and the patient 200 may be moved into the bore of the device, either on a surgical support 60 as shown in FIG. 1, or on a separate patient table that is configured to slide in and out of the bore. Further, although the imaging device 103 shown in FIG. 1 is located close to the patient 200 within the surgical theater, the imaging device 103 may be located remote from the surgical theater, such as in another room or building (e.g., in a hospital radiology department).

The motion tracking system 105 shown in FIG. 1 includes a plurality of marker devices 119, 202, 115 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The motion tracking system 105 in the embodiment of FIG. 1 includes a plurality of marker devices 119, 202 and 115 and a stereoscopic optical sensor device 111 that includes two or more cameras (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and 115 and received by the cameras. The marker devices 119, 202, 115 may each include three or more (e.g., four) reflecting spheres, which the motion tracking system 105 may use to construct a coordinate system for each of the marker devices 119, 202 and 115. A computer 113 may be coupled to the sensor device 111 and may determine the transformations between each of the marker devices 119, 202, 115 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, a reference marker device 115 (e.g., reference arc) may be rigidly attached to a landmark in the anatomical region of interest (e.g., clamped or otherwise attached to a bony portion of the patient's anatomy) to enable the anatomical region of interest to be continually tracked by the motion tracking system 105. Additional marker devices 119 may be attached to surgical tools 104 to enable the tools 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Each moiré pattern marker may also include a unique identifier or code that may enable different objects within the camera's field of view to be uniquely identified and tracked. An example of an MPT-based tracking system is available from Metria Innovation Inc. of Milwaukee, Wisconsin. Other tracking technologies, such as computer vision systems and/or magnetic-based tracking systems, may also be utilized.

The system 100 may also include a display device 121 as schematically illustrated in FIG. 1. The display device 121 may display image data of the patient's anatomy obtained by the imaging device 103. The display device 121 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 121, and may be shown overlaying the image data. In the embodiment of FIG. 1, the display 121 is located on a mobile cart 120. A computer 113 for controlling the operation of the display 121 may also be housed within the cart 120. In embodiments, the computer 113 may be coupled to the optical sensor device 111 and may also perform all or a portion of the processing (e.g., tracking calculations) for the motion tracking system 105. Alternatively, one or more separate computers may perform the motion tracking processing, and may send tracking data to computer 113 on the cart 120 via a wired or wireless communication link. The one or more separate computers for the motion tracking system 105 may be located on the imaging system 103, for example.

Figure 2:
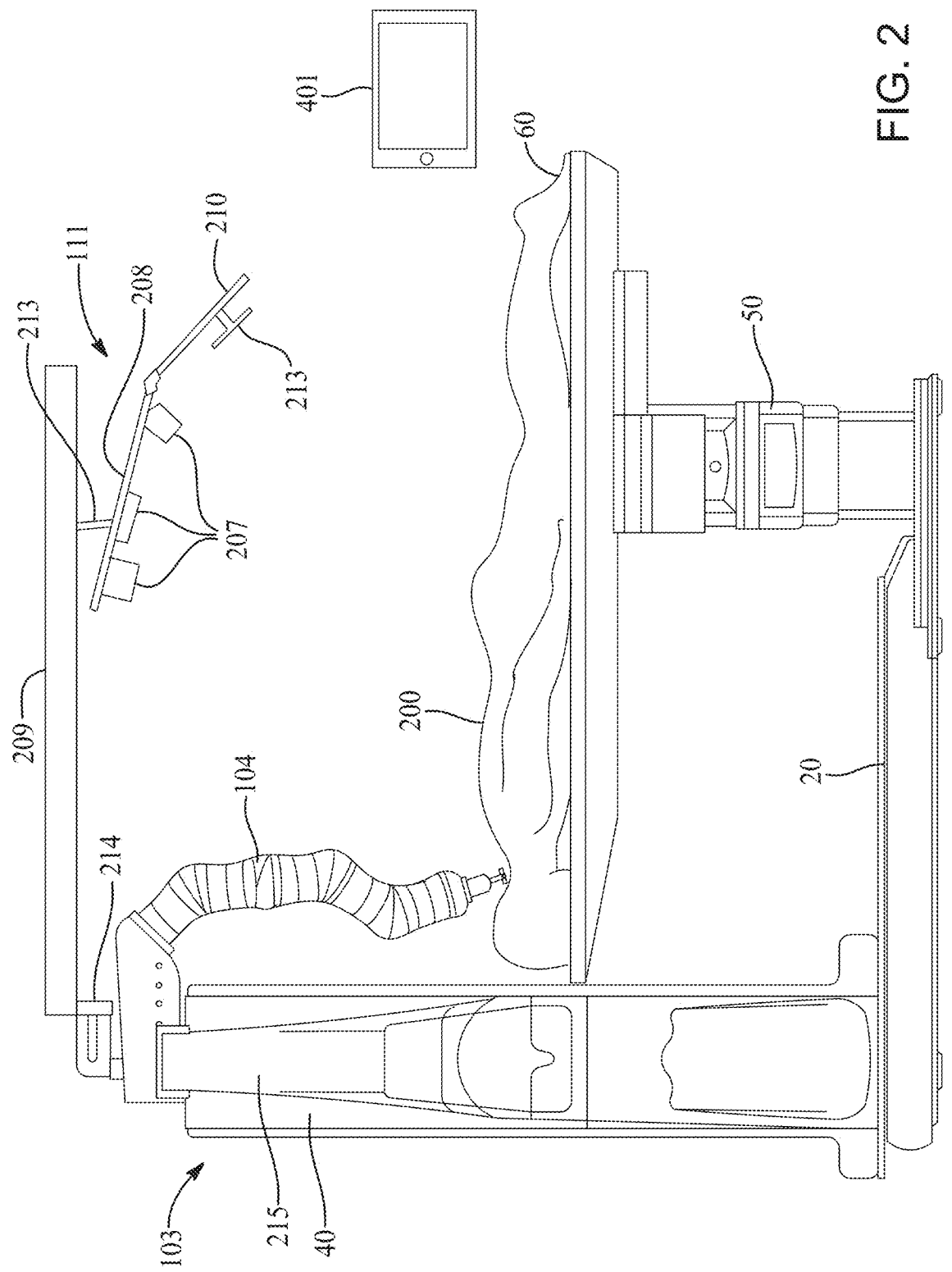
FIG. 2 shows an alternative embodiment of a system for performing robotically-assisted image-guided surgery having an optical sensing device for a motion tracking system on an arm extending from a gantry of an imaging system.

FIG. 2 illustrates an alternative embodiment of a system for performing robotically-assisted image-guided surgery according to various embodiments. In this embodiment, the optical sensor device 111 includes an array of cameras 207 mounted to a rigid support 208. The support 208 including the camera array is suspended above the patient surgical area by an arm 209. The arm 209 may be mounted to or above the imaging device 103. The position and/or orientation of the rigid support 208 may be adjustable with respect to the arm 209 to provide the camera array with a clear view into the surgical field while avoiding instructions. In embodiments, the rigid support 208 may pivot with respect to the arm 209 via a joint 213. In some embodiments, the position of the rigid support 208 may be adjustable along the length of the arm 209. A handle 210 attached to the rigid support 208 may be used to adjust the orientation and/or position of the optical sensor device 111. The optical sensor device 111 may be normally locked in place with respect to the arm 209 during an imaging scan or surgical procedure. A release mechanism 213 on the handle 210 may be used to unlock the optical sensor device 111 to enable its position and/or orientation to be adjusted by the user. In some embodiments, the arm 209 or a portion thereof may be pivotable with respect to the imaging system 103, such as via joint 214. In embodiments, the arm 209 may be raised or lowered relative to the top surface of the imaging system 103, and in some embodiments the entire arm 208 may reciprocate (e.g., to the left or right in FIG. 2) with respect to the imaging system 103.

In some embodiments, the rigid support 208 and cameras 207 may be removably secured to the arm 209 so that the support 208 and cameras 207 may be detached from the system for storage and/or transport. A docking system between the arm 209 and the rigid support 208 may provide mechanical coupling between the support 208 and the arm 209 and may also provide an electrical connection for data and/or power between the arm 209 and the array of cameras 207 mounted to the support 208.

FIG. 2 also illustrates a display device that may comprise a handheld display device 401. As used herein, "handheld computing device" and "handheld display device" are used interchangeably to refer to any one or all of tablet computers, smartphones, pendant controllers, cellular telephones, personal digital assistants (PDA's), netbooks, e-readers, laptop computers, palm-top computers, wearable computers, and similar portable electronic devices which include a programmable processor and memory coupled to a display screen and may include hardware and/or software to enable display of information, including patient information and/or images, on the display screen. A handheld computing device typically also includes an antenna coupled to circuitry (e.g., a transceiver) to enable wireless communication over a network. A handheld computing or display device may be characterized by a sufficiently compact and lightweight structure to enable a user to easily grasp, maneuver and operate the device using one or both hands.

A holder for a handheld computing device 401 may be in a suitable location to enable the user to easily see and/or interact with the display screen and to grasp and manipulate the handheld computing device 401. The holder may be a separate cart or a mount for the handheld computing device that may be attached to the patient support 60 or column 50 or to any portion of the imaging system 103, or to any of the wall, ceiling or floor in the operating room. In some embodiments, a handheld computing device 401 may be suspended from the arm 209 to which the optical sensing device 111 is attached. One or more handheld display devices 401 may be used in addition to or as an alternative to a conventional display device, such as a cart-mounted monitor display device 121 as shown in FIG. 1.

As shown in FIGS. 1 and 2, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted may be mounted to the same or a similar support element 215 (e.g., curved rail) as the robotic arm 101. The position of the robotic arm 101 and/or the support arm 209 may be adjustable along the length of the support element 215. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. In further embodiments, the robotic arm 101 and/or the optical sensing device 111 may be mounted to a separate mobile shuttle, as described in U.S. patent application Ser. No. 15/706,210, filed on Sep. 15, 2017, which is incorporated by reference herein. Although a single robotic arm 101 is shown in FIGS. 1 and 2, it will be understood that two or more robotic arms 101 may be utilized.

FIG. 3 is a process flow diagram that illustrates a method 300 of registering patient images. Computer-assisted surgery techniques generally utilize a process of correlating a dataset representing a portion of the patient's anatomy that is to be operated on with the position of the patient at the time of the surgical intervention. The position of the patient may be determined based on a second image dataset which may include real-time camera image(s) from a motion tracking system 105 as described above. The correlation between these datasets may be accomplished computationally using software, and may be referred to as "patient registration." The registration method 300 of FIG. 3 may be implemented using one or more computing devices, such as computer 113 shown in FIG. 1.

In block 301 of method 300, a first image dataset of the patient's anatomy may be obtained using an imaging device, such as the imaging device 103 shown in FIGS. 1 and 2. The first image dataset may be a three-dimensional dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). The first image dataset may be stored electronically in a memory. The first image dataset may be in any suitable format, such as in a file format that conforms to the Digital Imaging and Communications in Medicine (DICOM) standard.

In block 303 of method 300, a second image dataset of the patient and the surrounding patient space may be obtained using a motion tracking system, such as the motion tracking system 105 shown in FIGS. 1 and 2. The second image dataset may indicate the current position and/or orientation of the patient. The second image dataset may include at least one image of a marker device that may be obtained using an optical sensing device 111 (e.g., cameras 207). The marker device (e.g., reference arc 115) detected by the optical sensing device 111 may be in a known fixed relationship with the surgically-relevant portion of the patient's anatomy. The motion tracking system 105 may determine the transformation between the marker device 115 and the optical sensing device 111 (e.g., using well-known triangulation techniques), and may thereby determine the transformation between the sensing device 111 (e.g., camera 207 position) and the surgically-relevant portion of the patient's anatomy. The motion tracking system 105 may similarly determine transformations between each of the other marker devices (e.g., marker devices 119 and 202 in FIG. 1) and the optical sensing device 111. Each of the markers 115, 119 and 202 being tracked may then be placed within a common coordinate system. In embodiments, the common coordinate system may have an origin or zero point that may be considered to be fixed relative to the surgically-relevant portion of the patient's anatomy, and may also be referred to the patient coordinate system.

In block 305 of method 300, the first image dataset may be registered to the common coordinate system as the second image dataset (e.g., the patient coordinate system). This may include performing a rigid transformation to map each pixel or voxel of the first image dataset into corresponding 3D coordinates (i.e., x, y, z coordinates) of the common coordinate system. A number of techniques may be utilized for registering multiple image datasets. In one non-limiting example of a registration process for x-ray CT imaging data, a pre-scan calibration process may be used to precisely calculate (e.g., within 1 mm) the transformation between the isocenter of the x-ray gantry 40 and the optical sensing device 111. A set of markers 211 (e.g., 3 or more, such as 4-6 markers) may be provided on the surface of the gantry 40, as shown in FIG. 1. The markers 211 may be within the field of view of the optical sensing device 111 to enable the gantry 40 position to be tracked by the motion tracking system 105. A calibration phantom (not shown for clarity) having a marker device (e.g., similar to marker device 115 in FIG. 1) fixed thereto may be placed on the patient support 60 such that the marker device is also within the field of view of the optical sensing device 111. The motion tracking system 105 may determine the transformation between the gantry 40 coordinate system defined by the markers 211 and the optical sensing device 111 coordinate system as well as the transformation between the phantom coordinate system defined by the marker device on the phantom and the optical sensing device 111 coordinate system. These transformations may be used to determine the gantry-to-phantom transformation. The phantom may then be scanned using the imaging device 103. A set of elements (e.g., x-ray visible beads) that may be easily identified from the imaging data may be located in the phantom, where the geometry of these elements within the phantom coordinate system may be previously-known. An algorithm may be used to analyze the x-ray image data to identify the x-ray visible elements with respect to the center point of the image data, which corresponds to the isocenter of the gantry 40. Thus, the x-ray visible elements may be located in a coordinate system having an origin at the isocenter of the x-ray gantry 40, and the transformations between the isocenter and the phantom and the isocenter and the markers 211 on the gantry 40 may be calculated.

During a subsequent scan of the patient 200, the position and orientation of the patient 200 with respect to the isocenter of the imaging device 103 may be determined (i.e., by tracking the positions of the markers 211 on the gantry 40, which are known with respect to the isocenter, and the patient reference arc 115, which is known with respect to the surgically-relevant portion of the patient anatomy). This may enable the image data obtained during the scan to be registered into the patient coordinate system.

In an alternative embodiment, the position of the optical sensing device 111 may be known relative to the imaging system 103 with sufficient accuracy such that the image dataset of the patient's anatomy obtained using the imaging system 103 may be registered in the common coordinate system of the patient without the motion tracking system 105 needing to track the position or orientation of the imaging system 103. In embodiments, separate markers 211 on the gantry 40 of the imaging system 103 as shown in FIG. 1 may not be required or used. In some embodiments, the position of the optical sensing device 111 (e.g., the position of each of the cameras 207 as shown in FIGS. 1 and 2) may be known relative to the isocenter of the gantry 40 of the imaging system 103, such as via a calibration process that may be performed at the factory or during installation or pre-calibration of the system. The gantry 40 and/or the optical sensing device 111 may include keying features (e.g., high-precision bolt patterns) where the optical sensing device 111 attaches to the gantry 40 to ensure that the position of the sensing device 111 on the gantry 40 remains accurately fixed. In embodiments where the camera(s) 207 may be movable relative to the gantry 40, high-precision encoders may precisely record and correct for any changes in camera position/orientation relative to the isocenter of the gantry 40. During imaging scans, the optical sensing device 111 may track the position and orientation of the patient 200 with respect to the camera position, which is in a known, fixed geometric relationship with the isocenter of the imaging device 103. The image data obtained during a scan may thus be registered into the common coordinate system of the patient without needing to first perform a calibration scan on a phantom, as described above.

In block 307 of method 300, images of the patient's anatomy from the first image dataset may be displayed with an overlay of one or more features derived from the second image dataset in the common coordinate system. The images may be displayed on a suitable display device, such as display 121 shown in FIG. 1. The images of the patient's anatomy may include 2D slices of a three-dimensional image dataset (e.g., a tomographic reconstruction) and/or a 3D volume rendering of all or a portion of the image dataset. In embodiments, images obtained using multiple imaging devices or imaging modalities may be fused and displayed in a common coordinate system. For example, the first image dataset of the patient's internal anatomy may be an x-ray CT scan. Another image dataset of the patient's internal anatomy, such as an MRI scan, may be combined with the x-ray CT data and displayed on the display 121. The MRI scan data may be registered into the common coordinate system using a similar registration process as described above. Alternately or in addition, an algorithm for matching landmarks or fiducials identifiable from both image datasets may be used to merge the datasets for display.

The one or more features derived from the second image dataset that may be displayed overlaying the images of the patient's anatomy may include graphical depictions of a tool 104, an end effector 102 or another object that is tracked by the motion tracking system 105. The graphical depiction may be based on a known geometry of the tool 104, end effector 102 or another object. The graphical depiction may be a rendering of the actual size and shape of the object or may be a depiction of select features of the object, such as a location of a tip end of the object and/or an orientation of the object. The graphical depiction may also indicate a trajectory defined by the object (e.g., a ray extending from a tip end of the object into the patient) and/or a target point within the patient's anatomy that may be defined based on the position and/or orientation of one or more objects being tracked. In various embodiments, the tool 104 may be a pointer. The tool 104 may also be a surgical instrument, such as a needle, a cannula, dilator, a tool for gripping or cutting, an electrode, an implant, a drill bit, a screw, a screw driver, a radiation source, a drug and an endoscope. In embodiments, the end effector 102 of the robotic arm 101 may include a hollow tube or cannula that may be configured to hold one or more tools, such as a surgical instrument, and may be used to guide an instrument as it is inserted into the patient's body. Alternately, the end effector 102 itself may be or may include an instrument that may be inserted into the patient's body.

The motion tracking system 105 may repeatedly acquire new images from the optical sensing device 111, and the relative positions and/or orientations of objects within the field of view of the optical sensing device 111 may be updated with each acquisition of new images from the optical sensing device 111. The display 121 may be updated to reflect any change(s) in the position and/or orientation of the objects within the common coordinate system (e.g., relative to the patient reference arc 115), which may include adding additional graphical elements to depict new objects that are moved within the field of view of the optical sensing device 111 and removing graphical depictions of objects when they are no longer within the field of view of the optical sensing device 111. In some embodiments, the optical sensing device 111 may include a motorized system to enable the position and/or orientation of the camera(s) 207 to move to maintain the surgical area within the center of the field of view of the camera(s) 207.

Figure 4:
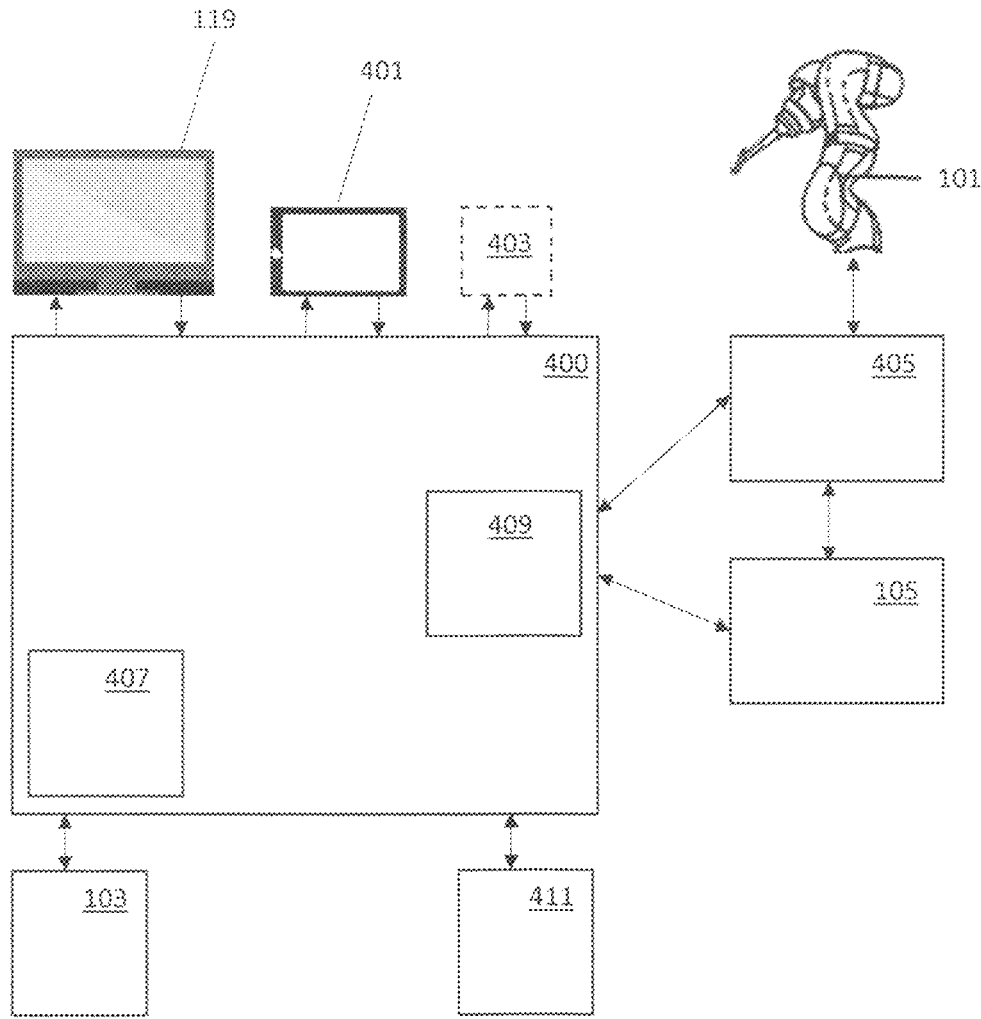
FIG. 4 is a block diagram schematically illustrating a system for robotically-assisted image-guided surgery according to an embodiment.

FIG. 4 is a component block diagram of an image-guided surgery system 400 according to an embodiment. The system 400 may be implemented using one or more computing devices, such as computer 113 shown in FIG. 1. The system 400 may be operatively coupled to a first display device 121, which may include a monitor that is fixed to a cart 120 or other structure (e.g., wall, ceiling, floor, imaging device, etc.) within the operating suite. The system 400 may also be operatively coupled to at least one additional display device 401, which may be a handheld computing device, as described above with reference to FIG. 2. The system 400 may also include an audio input/output component 403, which may include a speaker or other output component for outputting audible signals (e.g., audio instructions, alerts, etc.) and/or a microphone or other input component for receiving audio inputs (e.g., voice commands) that may be interpreted by the system 400. The system 400 may be implemented at least partially in software and may be based on one or more of the Image-Guided Surgery Toolkit (IG-STK), Visualization Toolkit (VTK) and Insight Segmentation and Registration Toolkit (ITK) development frameworks.

The system 400 may be configured to receive and store imaging data 407 (e.g., DICOM data) collected by an imaging device 103. The imaging data 407 may be received directly from the imaging device 103 or may be retrieved from another source, such as a remote server. The imaging data 407 may be imaging data that is obtained prior to a surgical procedure (e.g., pre-operative image data) and/or imaging data that is obtained during a surgical procedure (e.g., intra-operative image data). In embodiments, the system 400 may be configured to display the most-current image data 407 collected by the imaging device 103. The image data 407 may be registered to a common coordinate system as the tracking data 409 from the motion tracking system 105 in accordance with a registration method such as method 300 described above with reference to FIG. 3.

The system 400 may also receive tracking data 409 from a motion tracking system 105. The system 400 may be configured to repeatedly read the tracking data from the motion tracking system 105 indicating the current position/orientation of the patient and any other objects tracked by the motion tracking system 105. The system 400 may read the tracking data at a frequency (e.g., refresh rate) of greater than 100 Hz (e.g., 240 Hz). In embodiments, the tracking data from the motion tracking system 105 may include data to enable the system 400 to identify particular objects from within the tracking data. For example, each marker device (e.g., marker devices 115, 202 and 119 in FIG. 1) may include a unique characteristic (e.g., a unique geometric pattern of reflective markers, a unique flash pattern of active markers, etc.) to enable the marker device to be identified. These unique characteristics of the marker devices may be registered with particular objects or tools (e.g., associated with a particular object or tool in a database) by the system 400. The unique characteristics of the marker devices may be pre-registered in the system 400 and/or may be registered to particular objects or tools during the course of a surgical procedure.

In one embodiment, the image guided surgery system 400 may include an automatic identification and data capture (AIDC) component 411 that may be used during registration of surgical tools or instruments with unique marker devices. The AIDC component 411 may include a sensor device, such as an optical scanner, an RF receiver, a camera, etc. that may be configured to analyze a characteristic of the surgical tool (e.g., scan an identifying mark, such as a model or serial number, etched into the tool, scan a barcode, RFID tag or near-field communication (NFC) tag on the tool, analyze a geometric feature of the tool using machine vision, etc.) while the motion tracking system 105 identifies the marker device attached to the tool. The AIDC component may search a database to determine whether the surgical tool or instrument has been previously entered into the IGS system 400, and if so, the IGS system 400 may automatically register the marker pattern in association with the known surgical tool or instrument. This may improve workflow and patient safety by obviating the need for medical personnel to manually enter data to pre-register tools/instruments. In embodiments, the registration process for surgical tools may occur while the tool is placed within a calibration fixture that may be used to precisely determine one or more geometric characteristics of the tool, such as the location of the tip end of the tool relative to the marker device, that may be registered in association with the tool and the unique marker pattern during a surgical procedure.

The system 400 may also include a library of graphical elements that may be associated with particular objects or tools (e.g., in a database). The system 400 may display graphical elements associated with the objects or tools being tracked by the motion tracking system 105 in the common coordinate system with the image data on the display(s) 119, 401.

The system 400 may include a user-interface component that may control the display of system information and/or graphical user interface elements on the display(s) 119 and 401. The system 400 may further process and implement user commands received from user interface devices. A user interface device, may include, for example, a touchscreen user interface which may be integrated with a display device 119, 401. In embodiments, a user interface device may alternately or additionally include one or more of a button, a keyboard, a joystick, a mouse, a touchpad, etc. which may be located on a display device 119, 401 and/or on a workstation (e.g., a workstation located on a cart 120). In embodiments, the user interface device(s) may also include a microphone (e.g., audio input/output component 403) that may receive voice commands that may be interpreted by the system (e.g., using voice recognition software). The user commands received via one or more user input devices may enable a user to control various functions of the system 400, such as changing what is shown on the display(s) 119, 401 (e.g., displaying different image datasets, displaying different slice(s) and/or different 3D rendering(s) within an image dataset, zooming in or out of an image, displaying different menu options, returning to a home screen, etc.). In embodiments, the user commands may enable a user to set one or more trajectories and/or target locations within the patient's anatomy. The system 400 may store the positions and/or orientations of user-defined trajectories or target locations within the common coordinate system, and may display graphical representations of such trajectories or target locations on the display(s) 119, 401.

The user commands received by the system 400 may also include commands for controlling the operation of other components, such as the imaging device 103, the motion tracking system 105 and/or a robotic arm 101. For example, for a robotically-assisted surgical procedure, the user command may include an instruction to move a robotic arm 101 to a particular position and/or orientation. The instruction to move the robotic arm 101 may be based on a user interaction with image data of the patient's anatomy that is displayed on a display device 119, 401. For example, the user may use the display device 119, 401 to define a particular trajectory with respect to the patient's anatomy and may send an instruction for the robotic arm 101 to move such that that the end effector 102 of the robotic arm 101 is positioned along the defined trajectory.

A robotic control system 405 may control the movement of one or more robotic arms 101. The robotic control system 405 may receive sensor data indicating the current parameters of the robotic arm 101 (e.g., robot position, joint angles, measured axis forces, motor currents) and may send motor control signals to drive the movement of the arm 101. In embodiments, the motion tracking system 105 may track the position of the robotic arm 101 (e.g., via marker device 202 on or proximate to end effector 102 as shown in FIG. 1) to determine the position of the end effector 102 within the common coordinate system of the patient. A control loop, which may be executed using the image-guided surgery system 400, the motion tracking system 105 and/or the robotic control system 405, may continuously read the tracking data and the robot parameter data and may send instructions to the robotic control system 405 to cause the robotic arm 101 to move to a desired position and orientation.

In various embodiments, display device 119 may be a primary display device (e.g., a monitor) that may be connected to the image-guided surgery system 400 by a wired or wireless link. In one embodiment, the system 400 may stream video data to the display device 119 over a suitable video data interface (e.g., an HDMI interface) and may also exchange other signals with the display device over a separate data connection (e.g., a USB connection).

In various embodiments, display device 401 may be a handheld computing device. A handheld display device 401 may generally be smaller and lighter than the primary display device 119 (e.g., a monitor), and may in certain embodiments be referred to as a secondary display device. In some embodiments, display device 401 may be a mirror of display device 119 and may display all or a portion of the same information as is shown on display device 119. Alternately, display device 401 may display different information than is shown on display device 119. In some embodiments, display device 119 may be omitted, and handheld display device 401 may be the only display device operably connected to the image-guided surgery system 400. In such a case, display device 401 may be referred to as the primary display device. Further, although a single handheld display device 401 (i.e., a tablet computer) is shown in FIG. 4, it will be understood that multiple handheld display devices 401 may be simultaneously connected to and used with the system 400.

The handheld display device 401 may be coupled to the image-guided surgery system 400 by a wired or wireless communication link. In one embodiment, the handheld display device 401 may communicate with the system 400 over a wireless communication interface. The system 400 may stream digital video data (e.g., high-definition video) for display on the handheld display device 401, such as over a wireless local area network (WLAN) connection, including a IEEE 801.11 (e.g., WiFi) connection. The system 400 may also exchange other signals with the handheld display device 401 (e.g., control signals from the system 400 and/or user commands received at a user interface, such as a touchscreen, on the display device 401) over a wireless connection. The system 400 and the display device 401 may communicate over any suitable wireless protocol or standard, such as over a IEEE 802.15x (e.g., a BLUETOOTH®) connection.

An image-guided surgical system 400 according to various embodiments may provide a plurality of modes for displaying patient information. For example, a first display mode may include displaying a 3D image dataset (e.g., an x-ray CT, MRI, sonogram, PET or SPECT image dataset) in multiple two-dimensional slices corresponding to anatomic planes (e.g., axial, sagittal, coronal planes) transecting the patient. This is illustrated in the screenshot of a display device shown in FIG. 5. The display device may be a display device 119 (e.g., monitor) as shown in FIG. 1 or a handheld display device as shown in FIGS. 2 and 4. The display screen 500 in this example illustrates four different patient images in four quadrants of the display screen 500. Three of the quadrants (i.e., top left, top right and bottom left quadrants of display screen 500) depict different two-dimensional slices 501, 503, 505 of CT image data. A fourth quadrant (i.e., lower left quadrant of display screen 500) includes a 3D volume rendering 507 illustrating a "virtual" view of anatomic feature(s) (e.g., bony structures or other discrete internal anatomic features). The two-dimensional slices 501, 503, 505 correspond, respectively, to views taken along axial, sagittal and coronal planes through the patient 200.

Figure 5:
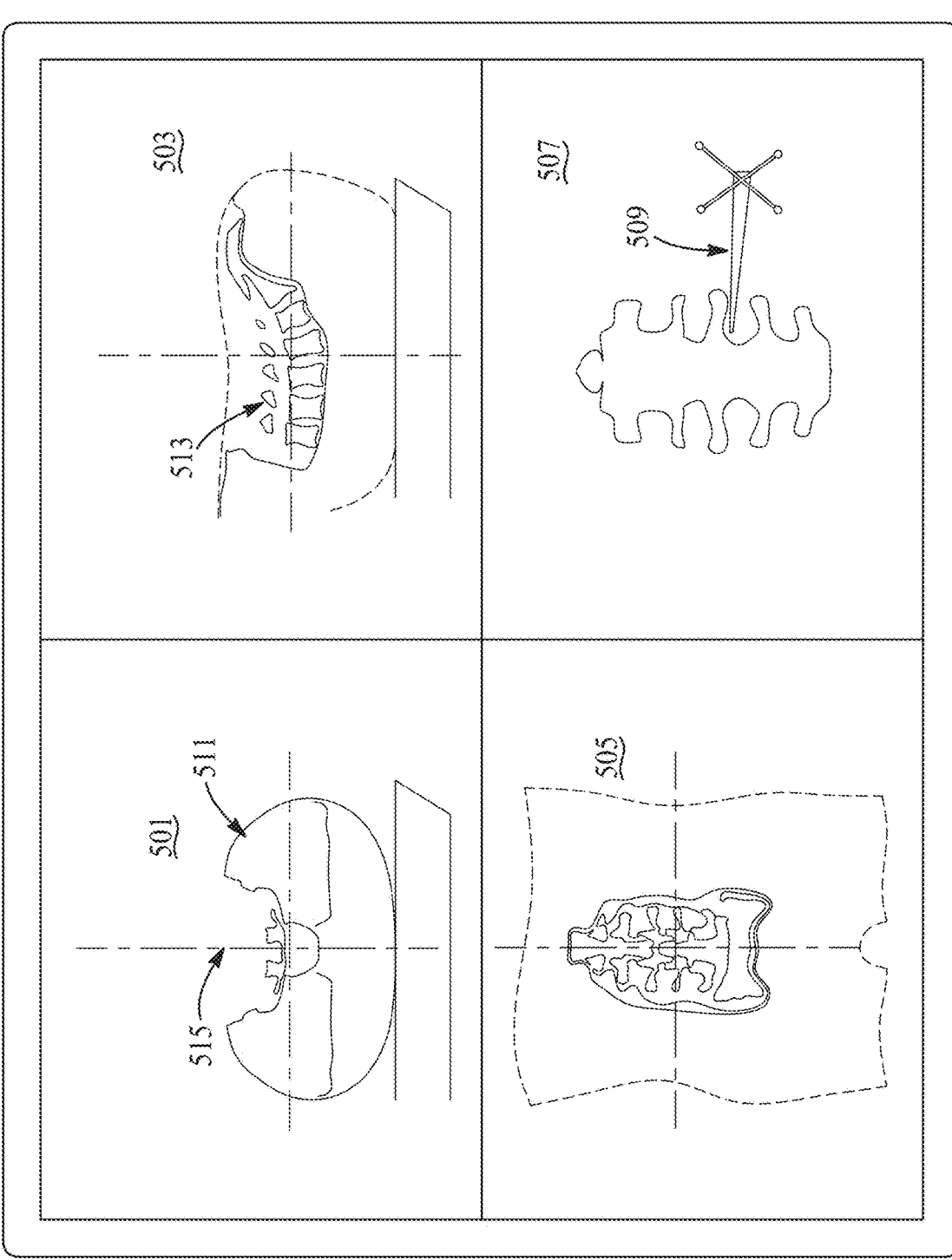
FIG. 5 illustrates a display screen of a display device in an image-guided surgery system according to an embodiment.

The display screen 500 may also display graphical elements illustrating the relationship of each slice 501, 503, 505 relative to the other slices shown on the display screen 500. For example, as shown in FIG. 5, the axial slice 501 image data may include an overlay of a cross pattern 515 showing the intersection of the axial slice 501 with the planes corresponding to the sagittal and coronal slices 503 and 505 shown on the display screen 500. Similar cross patterns 515 may be displayed overlaying the display of image data in the sagittal and coronal slices 503 and 505. The display screen 500 may also include graphical representations or renderings of other objects or tools tracked by the motion tracking system 105. In the example of FIG. 5, a graphical representation of a tool 509 is shown in the lower right quadrant of the display screen 500. The graphical representation of the tool 509 may illustrate the position and orientation of the tool relative to the anatomic features depicted in the 3D volume rendering 507. Similar graphical elements may be displayed in the 2D slice images 501, 503 and 505 to illustrate the position and/or orientation of one or more objects with respect to the patient.

It will be understood that the four-quadrant view shown in FIG. 5 is one possible implementation of a display of patient information on a display device 119, 401. Other possible display modes are possible. For example, rather than illustrating multiple different images (e.g., slices) from a patient image dataset (e.g., reconstructed volume), the display screen 500 may show only a single image (e.g., a single axial, sagittal or coronal slice 501, 503, 505 or a single 3D volume rendering 507). The display screen 500 may illustrate only two slices corresponding to different anatomic planes (e.g., axial and sagittal, axial and coronal, or sagittal and coronal slices), or may illustrate a single slice along with a 3D volume rendering. In some embodiments, the display screen 500 may illustrate multiple two-dimensional slices corresponding to the same anatomic planes (e.g., multiple axial, sagittal and/or coronal slices taken through different sections of the reconstructed volume) and/or multiple 3D volume renderings viewed from different angles. The display screen 500 may also display real-time video images of the surgical area. The real-time video images may be obtained from a camera located at a suitable location, such as a head-mounted camera worn by a surgeon and/or a camera mounted to a structure (e.g., on the optical sensing device 111, arm 209 or support element 215, on the imaging device 103, to the patient support 60, to a surgical light apparatus, or to any of to any of the wall, ceiling or floor in the operating room, or to a separate cart). The video images may also be images obtained from within the surgical site, such as from an endoscope inserted into the patient.

The different images and display modes of the display screen 500 may be customizable based on user selections, which may be made via a user input device and/or user voice commands. In embodiments, the user may be able to select (e.g., scroll through) different patient images, such as sequentially illustrating multiple axial, sagittal and/or coronal slices taken through different sections of the reconstructed volume, or sequentially illustrating multiple 3D volume renderings viewed from different angles. The display screen 500 may also display slices along oblique planes taken through the reconstructed volume. The user may also have the capability to control the magnification of images, such as by zooming into or out from a particular portion of an image shown in the display screen 500. The user may control the selection of patient images for display using a user input device, voice commands and/or via a separate tool, such as a pointer device. In some embodiments, the intersection of the three image planes (i.e., axial, sagittal and coronal) shown on the display panel 500 may coincide with a target position within the patient's body. The surgeon may use the display panel 500 as a "virtual cutting tool" to move through the various slices/views of the patient image volume and to identify and select a target region for a surgical intervention.

The user (e.g., a surgeon) may be able to set one or more target positions and/or trajectories within the patient 200. There may be a variety of ways to set a trajectory or target location. For example, the surgeon may move through different views of the patient image data by manipulating a tool (e.g., a pointer/stylus device and/or an end effector of a robotic arm) over the patient 200, where the tool may define a unique trajectory into the patient. The tool may be tracked within the patient coordinate system using the motion tracking system 105. In some embodiments, an imaginary ray projected forward from the tip end of the tool may define the unique trajectory into the patient, which may be graphically depicted on the display screen 500. A target location along the unique trajectory may be defined based on a predetermined offset distance from the tip end of the tool. Alternately, the surgeon may directly manipulate and interact with the displayed image data to identify a particular target or trajectory, such as using a workstation computer. A particular target point or trajectory may be set by the system 400 in response to an input event, which may include, for example, a voice command, a touch event on a touchscreen interface, and/or an input on a user interface device (e.g., a keyboard entry, a mouse click, a button push, etc.). In embodiments, the surgeon may set a target position and/or trajectory by interacting with image data displayed on a display device, such as display devices 119 and/or 401. For example, the surgeon may define a target point and/or trajectory in the patient 200 by selecting one or more points on a display screen 500 of a display device 119, 401 (e.g., marking the points using a stylus, a cursor or mouse pointer, or a touch on a touchscreen user interface). To define a trajectory, for instance, the user may select two or more points in the image data (e.g., a target point and an entrance point on the skin of the patient). In embodiments, the user may be able to make fine adjustments to a selected target point and/or trajectory using any suitable user interface device. Multiple target points and/or trajectories may be set and saved in a memory (e.g., in an image-guided surgery system 400 as illustrated in FIG. 4), where each target point and/or trajectory may be saved in association with a unique identifier (e.g., file name).

In embodiments, the display screen 500 may display graphical element(s) overlaying the image data corresponding to one or more target locations and/or trajectories that are set by the user. For example, defined target locations may be illustrated as identifiable dots or points in the image data, which may be color coded and/or labeled on the display screen 500 to enable easy visualization. Alternately or in addition, defined trajectories may be depicted as identifiable lines or line segments in the image data, which may be similarly color coded and/or labeled. As discussed above, the display screen 500 may also display graphical elements associated with particular tools or objects, including invasive surgical tools or instruments that are tracked by the motion tracking system 105. In embodiments, the display screen 500 may depict at least a portion (e.g., a tip end) of a surgical instrument as it is inserted into the patient 200, which may enable the surgeon to track the progress of the instrument as it progresses along a defined trajectory and/or towards a defined target location in the patient 200. In some embodiments, the patient images on the display screen 500 may be augmented by graphical illustrations of pre-calibrated tools or implants (e.g., screws) that are located within the patient 200.

The at least one robotic arm 101 may aid in the performance of a surgical procedure, such as a minimally-invasive spinal surgical procedure or various other types of orthopedic, neurological, cardiothoracic and general surgical procedures. In some embodiments, when the robotic arm 101 is pointed along a set trajectory to a target position, the robotic arm 101 may maintain a rigid or fixed pose to enable the surgeon to insert an instrument or tool through a cannula or similar guide arranged along a vector that coincides with the predefined trajectory into the body of the patient 200. The cannula may be a portion of the end effector 102 of the robotic arm 101 or it may be separate component that is held by the end effector 102. The cannula/guide may be positioned by the robotic arm 101 such that the central axis of the cannula is collinear with the predefined trajectory into the patient 200. The surgeon may insert one or more invasive surgical instrument through the cannula/guide along the trajectory and into the body of the patient to perform a surgical intervention. Alternately, the end effector 102 itself may comprise a surgical instrument that may be moved into the body of the patient, such as, without limitation, a needle, a dilator, a tool for gripping, cutting or ablating tissue, an implant, a drill bit, a screw, a screw driver, a radiation source, a drug and/or an endoscope.

Figure 6A:
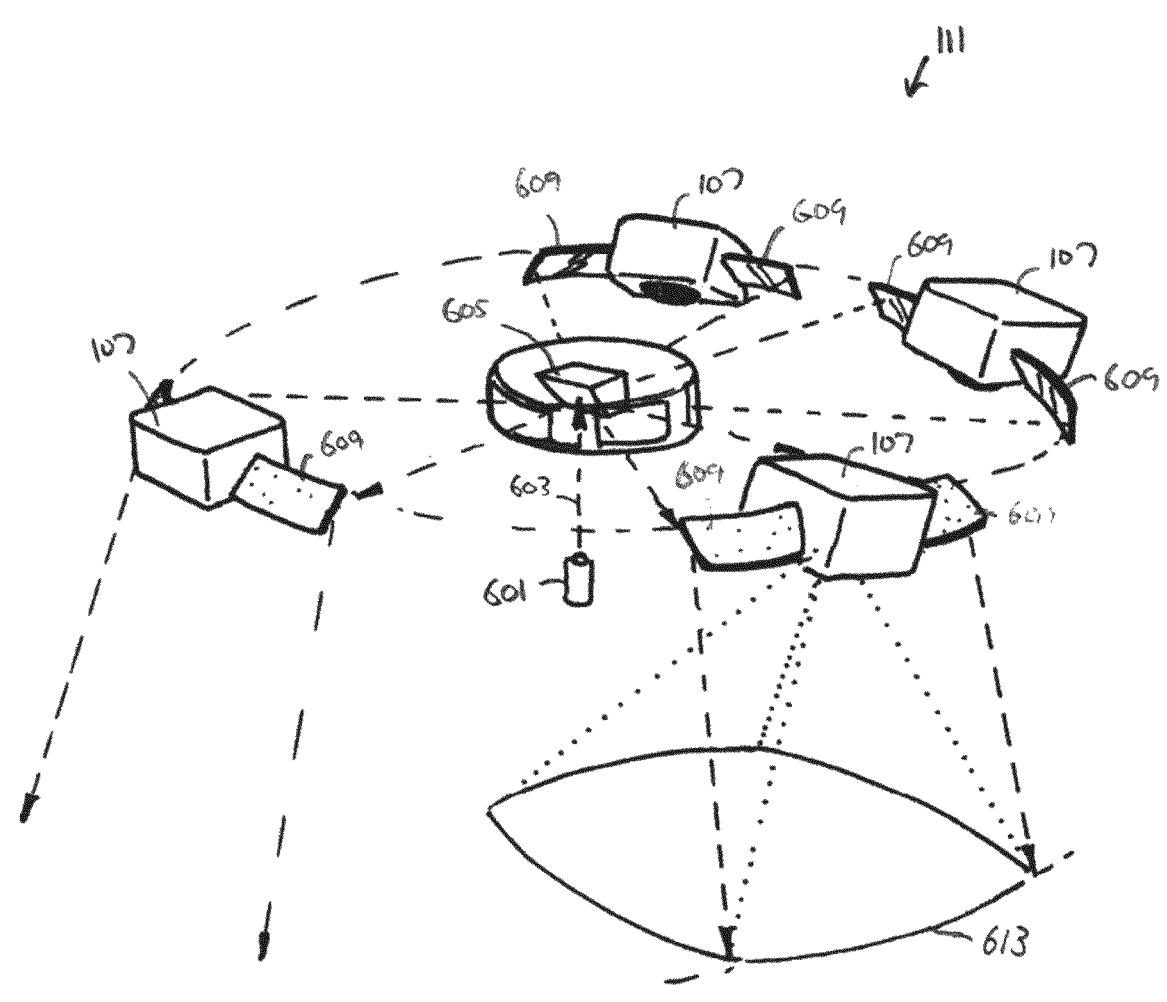
FIGS. 6A-6C schematically illustrate an image guided surgical system that includes an optical system for providing a visible indication of a range of a motion tracking system.
Figure 6B:
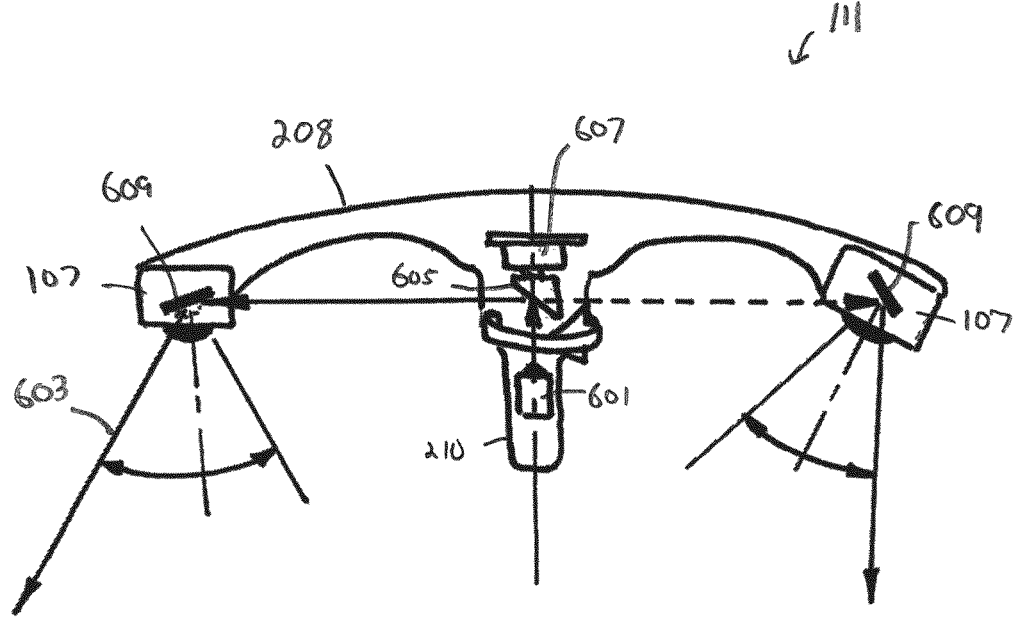

Various embodiments include an image guided surgery system that has an optical system that provides a visible indication of a range of a motion tracking system. In various embodiments, the optical system includes at least one light source that directs visible light to indicate a field-of-view of one or more optical sensing devices (e.g., cameras) of a motion tracking system. FIGS. 6A and 6B illustrate an example of an optical sensing device 111 of a motion tracking system 105, such as described above with reference to FIGS. 1 and 2. The optical sensing device 111 includes an array of multiple (e.g., four) cameras 107 mounted to a rigid support 208 (see FIG. 6B). The support 208 may be mounted above the surgical area, such as on an arm 209 as shown in FIG. 2. The support 208 in this embodiment includes a handle 210 that extends from the bottom of the support 208 that may be used to adjust the position and/or orientation of the optical sensing device 111.

As discussed above, an optically-based motion tracking system 105 may include a stereoscopic camera array that detects optical radiation (typically infrared (IR) radiation) from a plurality of marker devices. The markers may be active markers that include IR emitters or may be passive markers that reflect IR radiation from an external source, which may be co-located with the camera array. In either type of motion tracking system 105, it may be difficult for the user to determine which objects are within the field-ofview of the camera array at a given time (and thus are being tracked) and whether the cameras' line of sight to the surgical area is blocked by an obstruction.

Figure 6C:
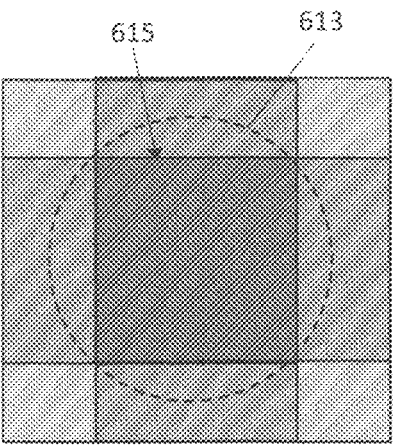

Embodiments include an optical system for providing a visible indication of the range of a motion tracking system 105, including a field-of-view of an optically-based motion tracking system. As shown schematically in FIGS. 6A-6B, an optical sensing device 111 includes a visible light source 601, which may be a laser source, mounted to the rigid support 208 that supports an array of cameras 107. Although a single visible light source 601 is shown in FIG. 6A, it will be understood that multiple visible light sources may be mounted to the support 208. In this embodiment, the visible light source 601 is mounted inside the handle 210 of the support 208. The visible light source 208 projects a beam 603 of radiation in a first (e.g., vertical) direction onto the surface of a rotating mirror 605, as shown in the partial cross-section view of FIG. 6B. The rotating mirror 605 redirects the beam 603 along a second (e.g., horizontal) direction that is substantially perpendicular to the first direction. A motor 607 mechanically coupled to the rotating mirror 605 rotates the mirror within the rigid support 208. The rotation of the mirror 605 causes the beam 603 to revolve around the support. A second set of mirrors 609 spaced radially from the rotating mirror 605 redirects the beam 603 along a third direction towards the surgical site. As shown in FIG. 6A, the second set of mirrors 609 may be adjacent to and optionally coupled to the cameras 107 of the camera array. Each of the mirrors 609 may have an angled or contoured surface that redirects the beam in the direction of the camera's 107 field of view. As the rotating mirror 605 rotates around the support 608, the beam 603 repeatedly traces a visible outline 613 on whatever surface(s) are located in front of the camera array. At a sufficiently high rate of revolution of the rotating mirror 605, the outline 613 may be continuously perceptible to the user. The second set of mirrors 609 may be calibrated so that the visible outline 613 generally corresponds to a boundary of a field-of-view of the camera array. For example, the visible outline 613 may be a circle or arc that encompasses an outer boundary of the camera's 607 field of view, as shown in FIGS. 6A-6B. In one embodiment shown schematically in FIG. 6C, the visible outline 613 traced by the beam may encompass a region 615 that is within the field of view of at least two cameras 107 of the camera array.

The visible light source 601 may also be a source of incoherent light, such as a light emitting diode (LED), as an alternative to a laser as described above. An advantage of a laser source is that may be used to create a sharply-delineated boundary. However, a drawback to the use of a laser light beam is that it may reflect off of shiny surfaces, including instruments, and can create safety issues. The visible light source 601 may be a high-intensity non-laser light source, such as an LED, which may be configured to reflect off of a 360-degree reflector to produce a disc of light. The 360-degree reflector may be an alternative to the rotating mirror 605 as described above. The disc of light from the reflector may be directed to reflect off the afore-mentioned angled or contoured mirrors 609 to project a pattern of illumination which overlaps the field-of-view of the cameras 107.

In embodiments, the optical sensing device 111 may be positioned to optimize the view of the cameras 107 into the surgical space. However, it may be desirable for the cameras 107 to also see marker devices that are located outside of the surgeon's work space, such one or more markers attached to the base end of the robotic arm 101 (e.g., to provide a "ground truth" measurement of robot position) and/or on the imaging device 103, such as the markers 211 on the gantry 40 used for scan registration as shown in FIG. 1. The cameras 107 may have a large enough field of view to see all of the markers if the cameras 107 are positioned far from the patient, but such a camera position may be sub-optimal for viewing and tracking instruments within the surgical area.

Figure 7A:
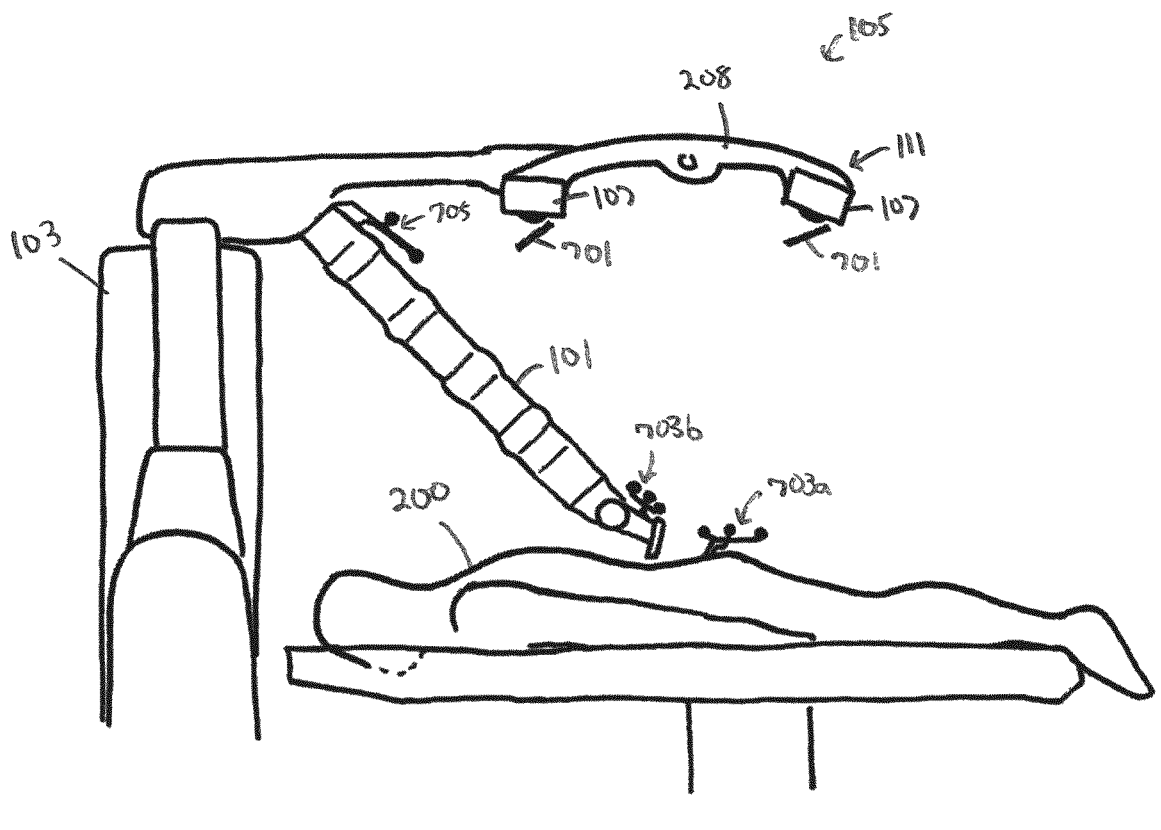
FIG. 7A schematically illustrates an optical sensing device for a motion tracking system that includes at least one beam splitter coupled to the optical sensing device for tracking markers located in multiple directions.

FIG. 7A illustrates an embodiment of an image guided surgery system that includes a motion tracking system 105 having an optical sensing device 111 as described above. The optical sensing device 111 includes an array of cameras 107 mounted to a rigid support 208. The support 208 may be mounted above the surgical area, with the cameras 107 pointed in a first direction to detect optical signals from one or more first marker array(s) 703a, 703b located in the surgical area. In the embodiment of FIG. 7A, marker arrays 703a, 703b are shown attached to the patient 200 and the robotic arm 101, respectively. The first marker array(s) may include active markers that emit their own optical signals (e.g., IR radiation), or passive markers that reflect optical signals from an external source. At least one beam splitter 701 is optically coupled to the optical sensing device 111. In the embodiment shown in FIG. 7A, each camera 107 of the optical sensing device 111 includes an associated beam splitter 701 positioned in front of the camera 107. The beam splitters 701 enable optical signals from the first marker array(s) 703a, 703b in the surgical area to pass through the beam splitters 701 along a first direction to be detected by the cameras 107. The beam splitters 701 are configured redirect optical signals received along a second direction from one or more second marker array(s) 705 located outside of the surgical area so that the signals may be received by the cameras 107. The one or more second marker array(s) 705 may be located on or proximate to the base end of the robotic arm 101 or on the imaging device 103, for example. The one or more second marker array(s) 705 may be referred to as reference markers that are located outside of the active surgical site.

In some embodiments, both the first marker array(s) 703a, 703b in the surgical area and the second marker array(s) 705 located outside of the surgical area may be active marker arrays. The operation of the marker arrays 703, 705 may be synchronized so that the cameras 107 receive signals from the first marker array(s) 703a, 703b and the second marker array(s) 705 at different times.

Alternately, the first marker arrays 703a, 703b and the second marker arrays 705 may be passive maker arrays that reflect IR radiation. The motion tracking system 105 may be configured to capture tracking data from the first direction and from the second direction at different times by, for example, projecting IR radiation along the first direction and along the second direction at different times.

In some embodiments, the motion tracking system 105 may be a hybrid system that utilizes both active and passive markers. In one example, the first marker array(s) 703a, 703b in the surgical area may be passive makers and the second marker array(s) 705 outside of the surgical area (e.g., at the base of the robotic arm 101 and/or the imaging system 103) may be active makers. The operation of the active second marker array(s) 705 may be synchronized with an IR source that projects IR radiation into the surgical area so that when the cameras 107 are receiving reflected radiation from the first marker array(s) 703a, 703b the second marker array(s) 705 are not emitting, and when the cameras 107 are receiving radiation emitted by the second marker array(s) 705 the IR source is not projecting into the surgical area.

As noted above, the optical sensing device 111 of the motion tracking system 105 may include a plurality of cameras 107 mounted to rigid support 208. The rigid support 208 may maintain the cameras 107 in a fixed relationship relative to one another. However, depending on how the rigid support 208 is mounted within the operating room, there can occur small movements (e.g., vibration, shaking, etc.) of the rigid support 208 and cameras 107 relative to the patient 200 and/or robotic arm 101. The optical sensing device 111 may also be repositioned by the user. The software of the motion tracking system 105 may not be able to distinguish between movements that are actual movements of the objects being tracked (such as marker arrays 703a, 703b within the surgical area) and an apparent movement of the tracked object(s) due to motion of the cameras 107 themselves. This may result in decreased accuracy of the surgical navigation and unnecessary movements of the robotic arm 101 to compensate for apparent motions of objects (such as the patient 200 and/or robotic arm 101) within the surgical field.

Figure 7B:
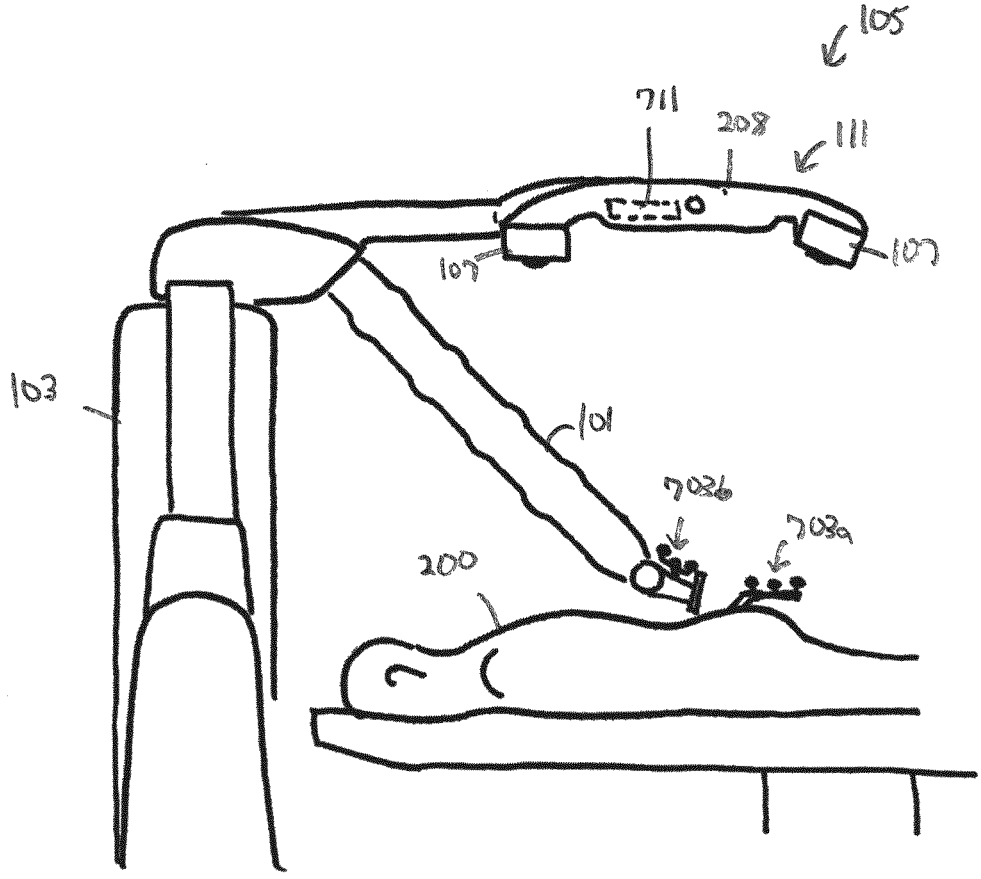
FIG. 7B schematically illustrates an optical sensing device for a motion tracking system that includes an inertial measurement unit attached to an optical sensing device to correct for movements of the optical sensing device.

FIG. 7B illustrates an embodiment of an image guided surgery system that includes a motion tracking system 105 having an inertial measurement unit 711 attached to an optical sensing device 111. The inertial measurement unit 711 may be mounted to the rigid support 208 on which an array of cameras 107 are mounted. The inertial measurement unit 711 may detect movements of the optical sensing device 111, such as a shaking or vibration of the rigid support 208 holding the cameras 107, or an intentional or accidental repositioning of the rigid support by a user. The measurements detected by the inertial measurement unit 711 may be sent to a processing device (e.g., a computer 113, such as shown in FIG. 1) along with tracking data from the optical sensing device 111. The measurements from the inertial measurement unit 711 may be utilized by motion tracking software implemented on the computer 113 to correct for detected movements of the optical sensing device 111 when tracking objects within the surgical area, including the patient 200, the robotic arm 101 and surgical tools. The inertial measurement unit 711 may provide an measurement of movement of the optical sensing device 111 that is independent of the tracking data obtained by the optical sensing device 111, which can aid the motion tracking system 105 in accurately differentiating between actual movements of the objects being tracked from apparent movements of the objects due to motion of the optical sensing device 111 itself.

The inertial measurement unit 711 may include a three-axis accelerometer and a three-axis gyroscope. The accelerometer and gyroscope may be fabricated utilizing MEMS technology. The accelerometer and gyroscope may be separate components (e.g., chips) located in the rigid support 208 or may be integrated on a single device (e.g., integrated circuit). The inertial measurement unit 711 may also include circuitry coupled to the accelerometer and gyroscope that may be configured to read output signals from these components. The accelerometer may output signals measuring the linear acceleration of the rigid support 208, preferably in three-dimensional space. The gyroscope may output signals measuring the angular velocity of the rigid support, preferably also in three-dimensional space. The signals from the accelerometer and gyroscope may be processed using a suitable processor, such as a computer 113 shown in FIG. 1, to determine the position and orientation of the rigid support 208 with respect to an initial inertial reference frame via a dead reckoning technique. In particular, integrating the angular velocity measurements from the gyroscope may enable the current orientation of the rigid support 208 to be determined with respect to a known starting orientation. Integrating the linear acceleration measurements from the accelerometer may enable the current velocity of the rigid support 208 to be determined with respect to a known starting velocity. A further integration may enable the current position of the rigid support 208 to be determined with respect to a known starting position.

In embodiments, measurement data from the inertial measurement unit 711 may transmitted from the optical sensing device 111 to a separate computing device (e.g., computer 113) via a wired or wireless link. The measurement data from the inertial measurement unit 711 may be sent via the same communication link as the tracking data from the cameras 107, or by a different communication link.

Although the embodiment of FIG. 7B illustrates an inertial measurement unit 711 located on the rigid support 208 holding the cameras 107, it will be understood that the inertial measurement unit 711 may be located on a camera 107. Each camera 107 may include an inertial measurement unit 711 that measures the motion of the camera 107 to correct for camera movement in the motion tracking system 105.

Figure 8A:
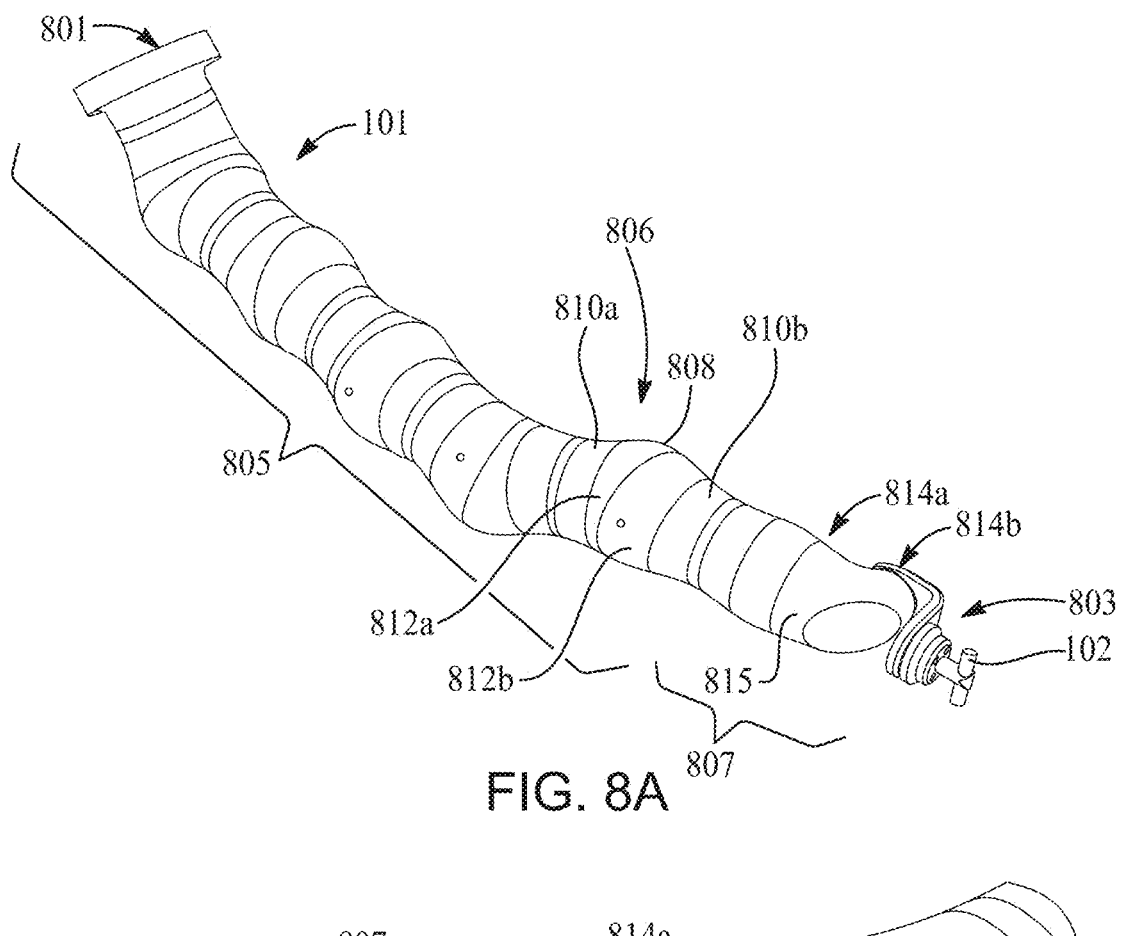
FIGS. 8A-8E illustrate robotic arms, including marker devices attached to a robotic arm.

FIG. 8A illustrates an embodiment of a robotic arm 101 for use in robotic-assisted surgery. The robotic arm 101 includes a base end 801 and a distal end 803, with an end effector 102 located at the distal end 803. As discussed above, the end effector 102 may comprise a cannula or guide that may be used to insert an invasive surgical tool or instrument along a trajectory into the patient, or alternately, the end effector 102 itself may comprise an invasive surgical instrument. During a surgical procedure, the robotic arm 101 may be covered in a surgical drape to maintain a sterile surgical field. The end effector 102 may be a sterile component that may be attached (e.g., snapped into) the distal end 803 of the robotic arm 101, optionally over the surgical drape.

The robotic arm 101 in this embodiment includes a first portion 805 that includes at least one 2-DOF joint 806. As used herein a "2-DOF joint" is a joint that enables robot articulation in two mutually orthogonal directions (i.e., pitch and yaw rotation). A 2-DOF joint is in contrast to a conventional (i.e., 1-DOF) robotic joint that rotates within a single plane. In the embodiment of FIG. 8A, the first portion 805 of the robotic arm 101 includes a chain of five 2-DOF joints 806 extending from the base end 801 of the robotic arm 101, although it will be understood that the first portion 805 may have more or less 2-DOF joints 806. The 2-DOF joints 806 may be modular in design, with each joint 806 including a central section 808 having a generally spherical outer surface between a pair of end sections 810a, 810b. The end sections 810a, 810b of adjacent joints 806 may be connected. The central section 808 may include a pair of wedge segments 812a, 812b having angled interfacing surfaces so that the rotation of the wedge segments 812a, 812b relative to one another produces pitch and yaw rotation of end section 810b relative to end section 810a over a particular angular range (e.g., ±15 degrees, such as ±20 degrees, ±30 degrees, ±45 degrees and ±100 degrees or more). Motors (not illustrated) mounted to the end sections 810a, 810b may drive the rotation of the wedge segments 812a, 812b. A universal joint (not visible) located inside the central section 808 and coupled to the end sections 810a, 810b may inhibit twisting motion of the end sections 810a, 810b.

Figure 8B:
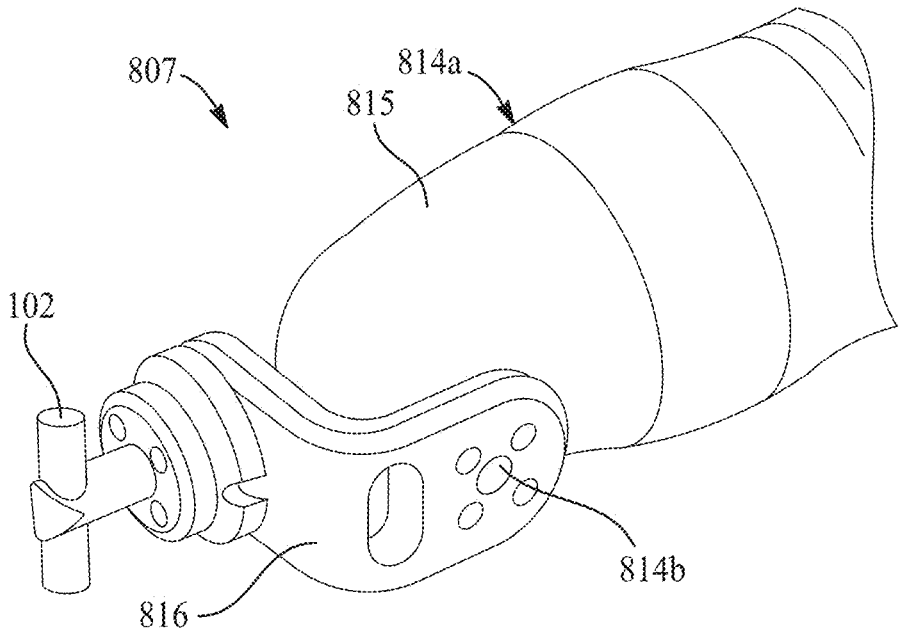

The robotic arm 101 in FIG. 8A may also include a second portion 807 that includes at least two rotary joints 814a, 814b (i.e., 1-DOF joints) that rotate about mutually perpendicular axes. The second portion 807 may include a housing 815 that includes motors (not visible) for driving the rotation of joints 814a and 814b. The second portion 807 may be located between the first portion 805 and the end effector 102 of the robotic arm 101. Joint 814a may be a theta wrist joint that may rotate the entire housing 815 with respect to the end section 810b of the adjacent 2-DOF joint 806. In embodiments, joint 814a may rotate continuously (e.g., >360°) in either direction. Joint 814b may be a wrist joint located on the side of the housing 815. Joint 814b may rotate the end effector 102 at least about ±45 degrees, such as ±90 degrees, ±120 degrees, ±170 degrees or more with respect to the housing 815. In one embodiment illustrated most clearly in FIG. 8B, a connector 816 between the joint 814b and the end effector 102 may align the end effector 102 with the midline of the housing 815 so that the rotation of the end effector 102 via joint 814b is in the same plane as the axis of rotation of theta wrist joint 814a. Alternately, the end effector 102 may rotate in a plane that is off-set from the axis of joint 814a, as shown in the embodiment of FIGS. 8D-8E.

Further embodiments include marker arrays for tracking the position and/or orientation of an end effector 102 of a robotic arm 101 using a motion tracking system 105. It may be desirable to provide a marker array that is proximate to the end effector 102 of the robotic arm 101 to maximize the accuracy of the positioning of the end effector 102. Conventional marker arrays include rigid frames having marker elements affixed thereon. Such arrays may project into the surgeon's workspace and may interfere with a surgical procedure.

Figures 8C, 8D:
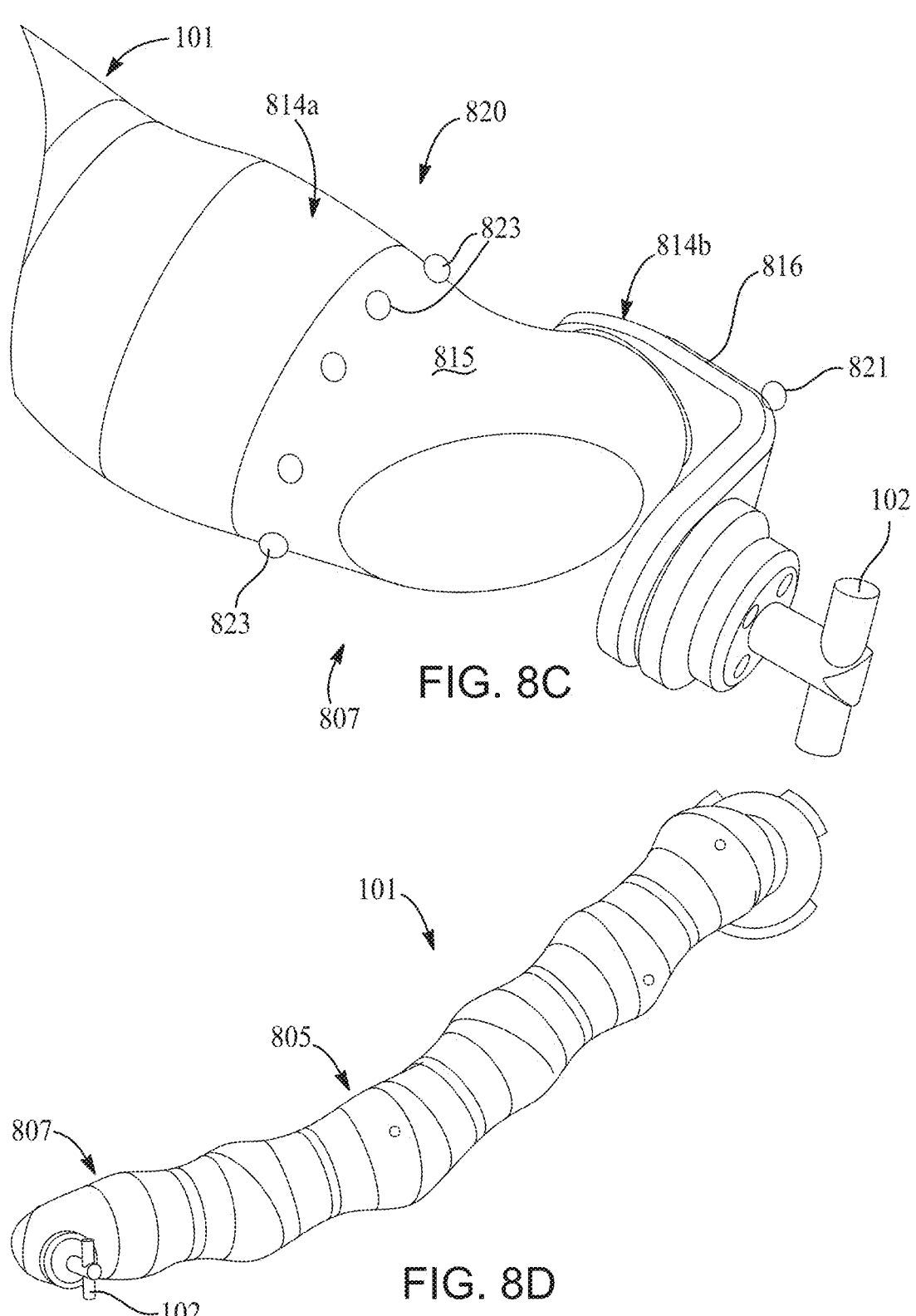
Figure 8E:
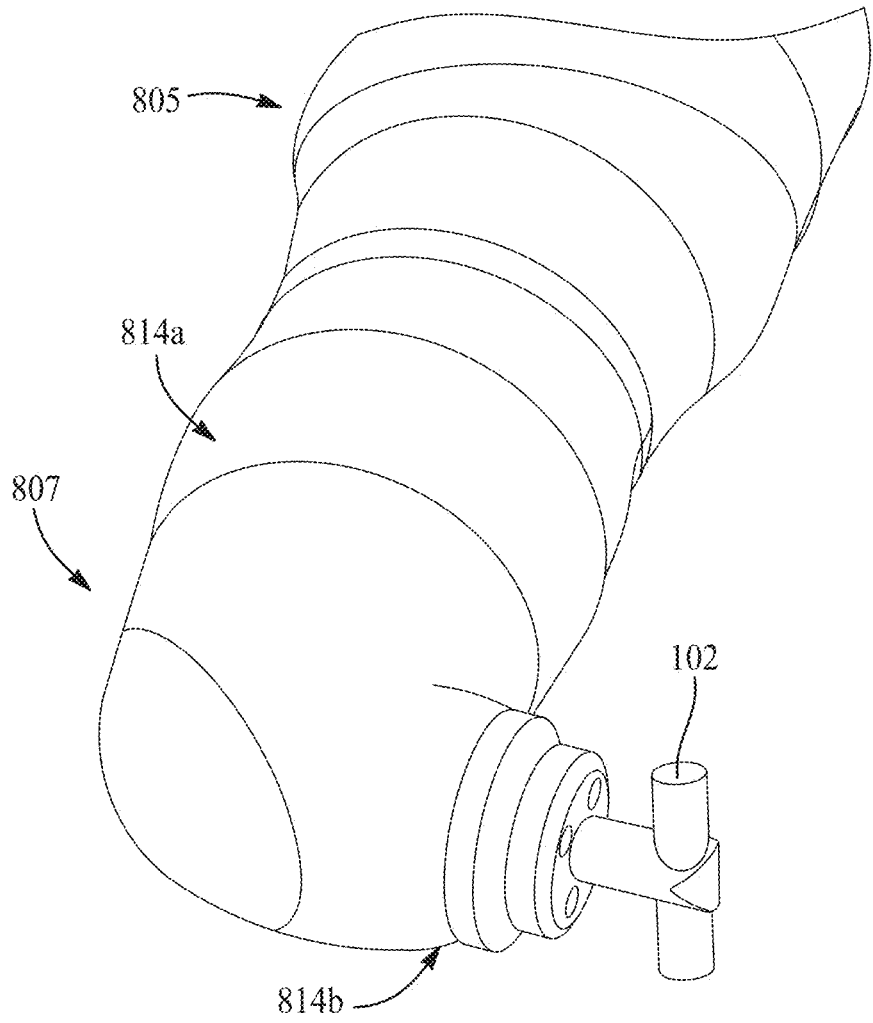

In the embodiment shown in FIG. 8C, a marker array 820 includes a plurality of marker elements attached to the robotic arm 101, and in particular, a plurality of marker elements attached to the second portion 807 of the robotic arm 101 proximate to the end effector 102. The marker array 820 includes a first set of one or more markers 821 located distal to the most distal joint 814b of the robotic arm 101 and a second set of one or more markers 823 located proximal to the most distal joint 814b of the robotic arm 101. Together, the first and second sets of markers 821, 823 form a marker array 820 that may be tracked by a motion tracking system 105 as described above.

In the embodiment of FIG. 8C, the second set of markers includes a plurality of markers 823 that may be secured to the housing 815 of the second portion 807 of the robotic arm 101. The second set of markers 825 may be spaced circumferentially around the housing 815. The first set of markers includes a single marker 821 that is located distal to the most distal joint of the robotic arm (i.e., joint 814b). Marker 821 may be located on the connector 816 that connects joint 814b to the end effector 102. Alternately, marker 821 may be located on the end effector 102 itself. Although the embodiment of FIG. 8C illustrates the first set of markers as consisting of a single marker 821, it will be understood that a plurality of markers 821 may be located distal to joint 814b.

The second set of markers 823 may be disposed in a geometric pattern that may be detected by the motion tracking system 105 and used to determine both the position of the robotic arm 101 in three-dimensional space as well as the rotational position of theta wrist joint 814a. As the end effector 102 is rotated on joint 814b, the change in relative position of the first set of marker(s) (i.e., marker 821 in FIG. 8C) to the second set of markers 823 detected by the motion tracking system 105 may be used to accurately determine the position and orientation of the end effector 102. The markers 821, 823 may be relatively unobtrusive so as not to interfere with the patient or the surgeon's work space.

In some embodiments, the markers 821, 823 attached to the robotic arm 101 may be active (i.e., light emitting) markers. The electrical power for light-emitting elements of the markers 821, 823 may be provided through the robotic arm 101. Alternately, the markers 821, 823 may be passive markers (e.g., spherical elements having a retroflective coating) that reflects light from an external source.

Figure 9A:
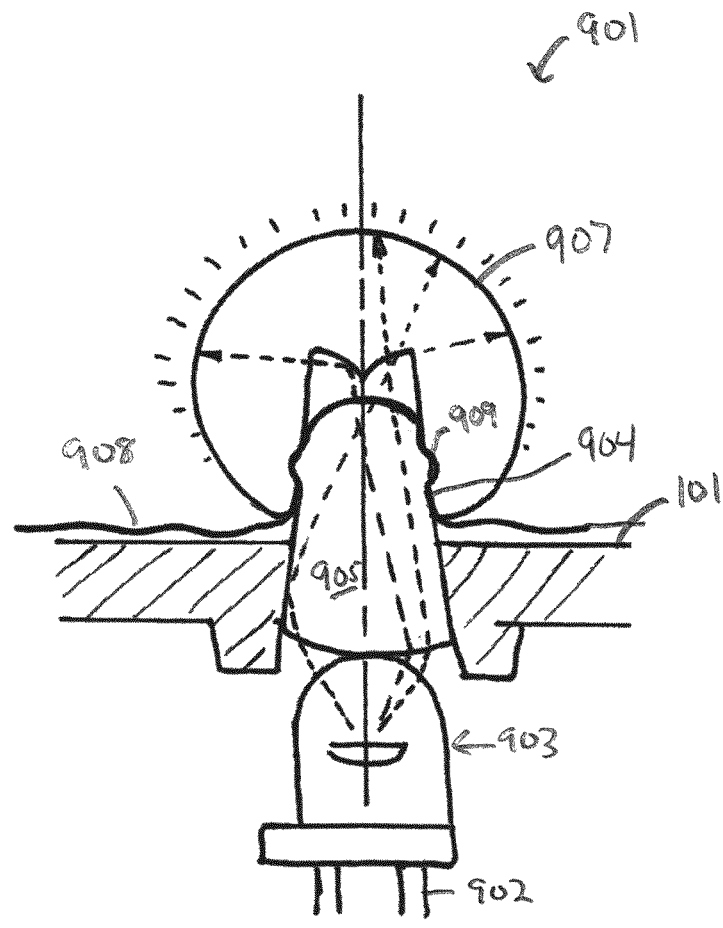
FIGS. 9A-9B illustrate marker devices on a robotic arm.
Figure 9B:
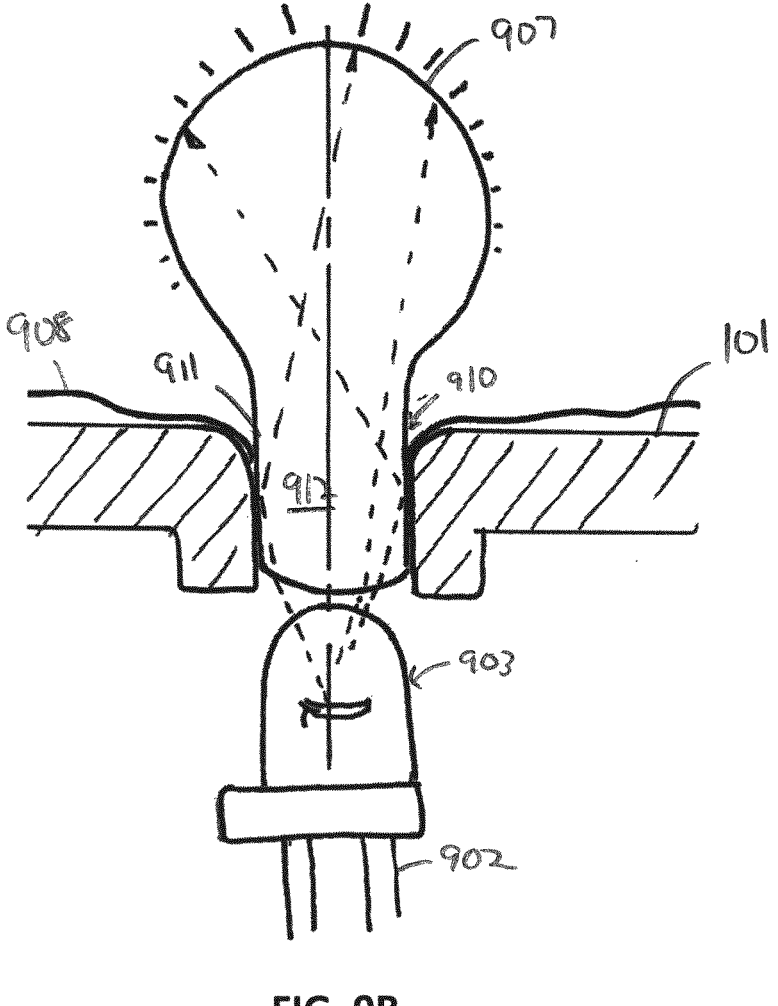

FIGS. 9A and 9B illustrate embodiments of an active marker device 901 that is located on a robotic arm 101. Power for the marker device 901 may be provided via a conductor 902 through the robotic arm 101 to a light source 903 (e.g., an LED source that emits light in an infrared (IR) wavelength range). In the embodiment of FIG. 9A, a projection 904 comprising an optical guide 905 (e.g., a light pipe) projects from the surface 906 of the robotic arm 101. Light from the light source 903 is coupled into the optical guide 905 and is transmitted through the projection 904. An optical diffuser 907 is attached to the projection 904 over the optical guide 905 and scatters the light as it emerges from the guide 905. In the embodiment shown in FIG. 9A, the robotic arm 101 is covered by a surgical drape 908. The surgical drape 908 is at least partially light-transmissive. The diffuser 907 may be attached to the projection 904 over the surgical drape 908. Mating features 909 on the projection 904 and the diffuser 907 may enable the diffuser 907 to snap on to the projection 904 over the surgical drape 908, which may be held tight against the projection 904. The diffuser 907 may be a sterile component, and may be a single-use disposable component.

FIG. 9B illustrates an alternative embodiment in which the robotic arm 101 includes a recessed portion 910, and the optical diffuser 907 includes a projection 911 that may be inserted into the recessed portion 910 to secure the diffuser 907 to the robotic arm 101. The diffuser 907 may be inserted over a surgical drape 908. Light from the light source 903 may be directed through the bottom of the recessed portion 910 and coupled into an optical guide 912 in the projection 911 of the optical diffuser 907. The projection 911 and the recessed portion 910 may optionally have mating features such as shown in FIG. 9A that secure the optical diffuser 907 to the robotic arm 101. As in the embodiment of FIG. 9A, the diffuser 907 may be a sterile component, and may be a single-use disposable component.

FIGS. 10A-10E illustrate various embodiments of an active marker array 1001 that may be used to track various objects and tools during image guided surgery. For example, the marker device 1001 may be a reference marker device that is attached to the patient (e.g., reference marker device 115 as shown in FIG. 1), it may be a marker device that is attached to a surgical tool or instrument (e.g., marker device 119 as shown in FIG. 1), and/or it may be a marker device that is attached to a robotic arm 101 for robot-assisted surgery (e.g., marker device 202 as shown in FIG. 1).

In general, an active marker device 1001 according to various embodiments includes a rigid frame 1003, an electronics module 1005 that includes at least one light source 1006 (e.g., an LED that emits light in an infrared range), and an optical guide apparatus 1007 that couples light from the at least one light source 1006 to an array of emitter locations 1008 on the rigid frame 1003. In embodiments, the rigid frame 1003 may be made (e.g., machined) to precise dimensions and tolerances out of metal or another suitable structural material. The rigid frame 1003 may include a network of channels 1009 extending within the rigid frame 1003. The optical guide apparatus 1007 may be located within the channels 1009. The channels 1009 may terminate in openings 1011 in the frame 1003 which may define the emitter locations 1008 of the marker device 1001.

Figure 10A:
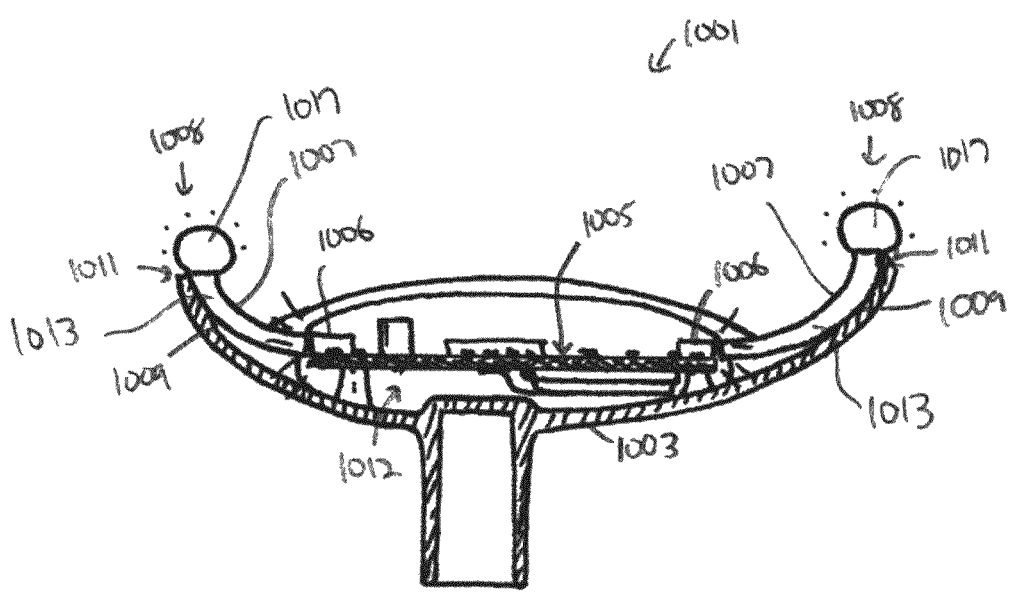
FIGS. 10A-10D illustrate various embodiments of an active marker device for a motion tracking system.

FIG. 10A is a side cross-sectional view of an active marker device 1001 according to an embodiment. In this embodiment, the frame 1003 may include a recess 1012 or housing within which the electronics module 1005 may be located. In addition to the at least one light source 1006, the electronics module 1005 may also include a power source (e.g., a battery) and circuitry for controlling the operation of the at least one light source 1006. For example, the circuitry may control the at least one light source 1006 to emit light having a particular pulse pattern or frequency. In embodiments, the circuitry may comprise or include a programmable microprocessor. The electronics module 1005 may also include communications circuitry, such as an RF receiver and/or transmitter, to enable communication with an external device, such as computer 113 in FIG. 1. In embodiments, the electronics module may communicate with an external device for synchronization of the pulsing of the light source and/or for setting or programming a particular pulse pattern. In embodiments, the electronics module 1005 may be located within a sealed housing or package. The power source may be a rechargeable battery, and in embodiments may be recharged wirelessly (e.g., via inductive charging).

The optical guide apparatus 1007 in this embodiment comprises a plurality of light pipes 1013. The light pipes may be made of a thermoplastic material (e.g., polycarbonate) and may be at least partially flexible or deformable. Alternately, the optical guide apparatus 1007 may comprise a plurality of optical fibers. The optical guide apparatus 1007 may comprise a unitary component. The optical guide apparatus 1007 may be separate from the electronics module 1005 or may be integral with the electronics module 1005. For example, the electronics module 1005 may be formed as a flex circuit such as shown in FIG. 10C, where a plurality of light pipes 1013 or similar optical guides may extend from the flex circuit.

Figure 10B:
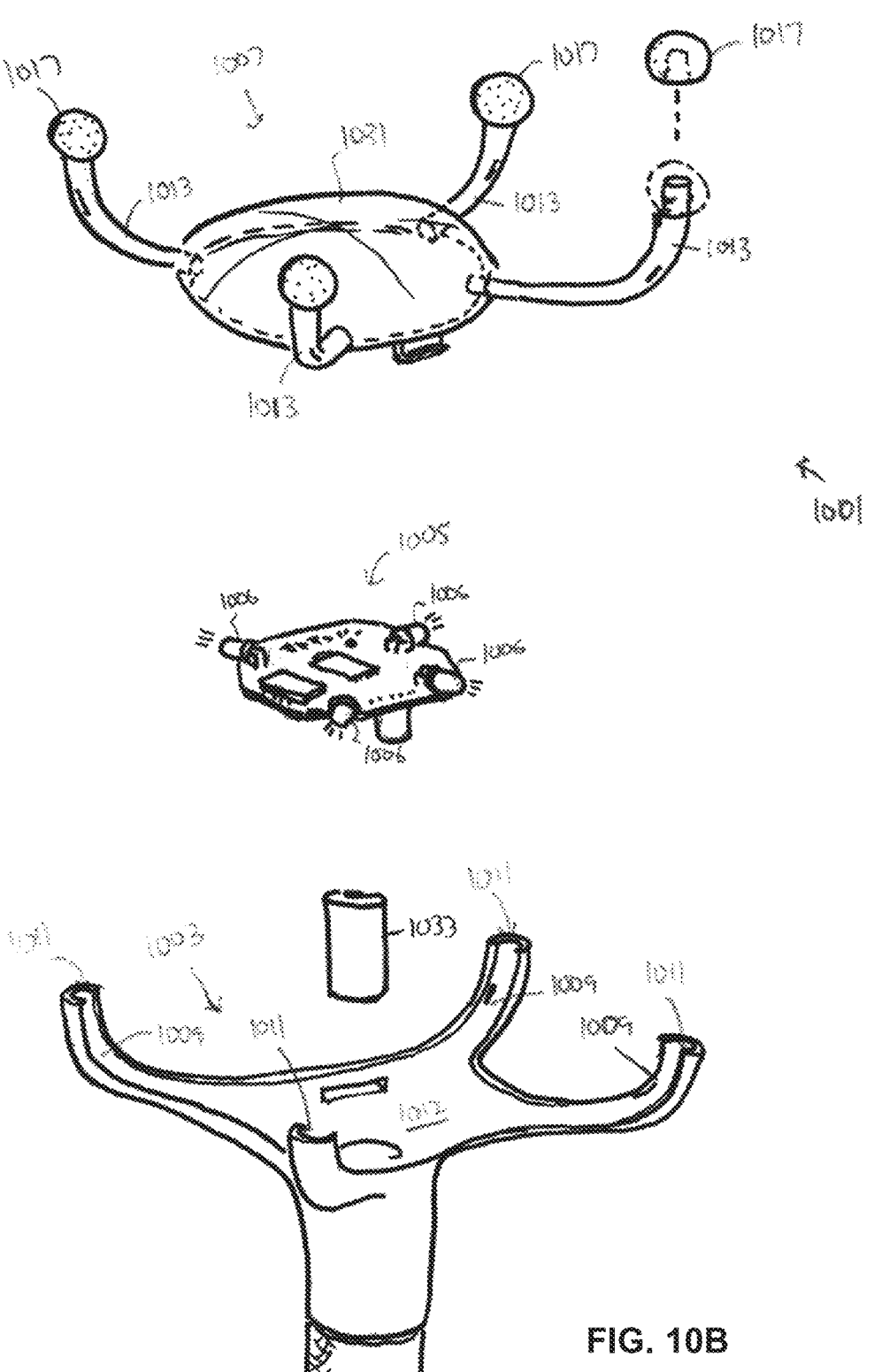
Figure 10C:
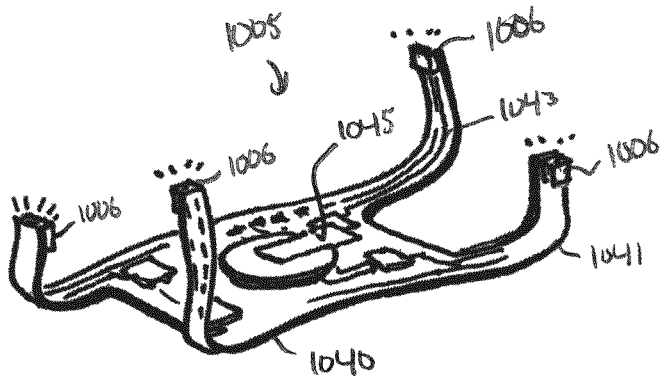

FIG. 10B is an exploded view of an active marker device 1001, including a rigid frame 1003, an electronics module 1005, and an optical guide apparatus 1007. In this example, the optical guide apparatus 1007 includes a plurality of light pipes 1009 extending from a protective cover 1031. The cover 1031 can attach to (e.g., snap into) the rigid frame 1003 to enclose the electronics module 1005 within a recess 1012 in the rigid frame 1003. In some embodiments, the electronics module 1005 may be attached to the protective cover 1031 so that the electronics module 1005 and optical guide apparatus 1007 form an integral component.

Alternatively, the electronics module 1005 may be a separate component that may be inserted within the recess 1012 of the rigid frame 1003, and the optical guide apparatus 1007 may be attached over the electronics module 1005. FIG. 10B also illustrates a separate power source 1033 (e.g., battery) for the electronics module 1005 that may be housed within the rigid frame 1003. Alternately, the power source 1033 may be integrated with the electronics module 1005.

The optical guide apparatus 1007 may be positioned within the frame 1003 such that light from the at least one light source 1006 of the electronics module 1005 is coupled into the light pipes 1013 of the optical guide apparatus 1007. Each of the light pipes 1013 may be inserted within a respective channel 1009 of the frame 1003. The light pipes 1013 may terminate proximate to the respective openings 1011 of the frame 1003 corresponding to the emitter locations 1008. In embodiments, optical diffusers 1017, which may be similar to the diffusers 907 described above in connection with FIGS. 9A-9B, may be located at the ends of the light pipes 1013 and over the openings 1011 in the rigid frame 1003. The diffusers 1017 may be integrated with the optical guide apparatus 1007 or may be snap-on components that attach over the ends of the light pipes 1013 and/or the openings 1011 in the rigid frame 1003.

FIG. 10C illustrates an alternative embodiment of an electronics module 1005 for an active marker device 1001 that is formed as a flex circuit. The electronics module 1005 includes a flexible substrate 1040 on which is located circuitry 1045 for controlling the operation of at least one light source 1006. The circuitry 1045 may contain, for example, a programmable microprocessor, and may also include communications circuitry, such as an RF receiver and/or transmitter, and an integrated power source as described above. The flexible substrate 1040 includes a plurality of peripheral arm regions 1041, each having a light source 1006 (e.g., LED) attached thereto. Electrical conductors 1043 may extend along the arm regions 1041 to connect each of the light sources 1006 to the rest of the circuitry 1045. The light sources 1006 may be located on or proximate to the distal ends of the arm regions 1041. The electronics module 1005 as shown in FIG. 10C may be inserted into a rigid frame 1003, such as shown in FIGS. 10A-B. The arm regions 1041 may extend along channels 1009 in the rigid frame 1003 so that each light source 1006 is aligned with a respective opening 1011 of the frame 1003 corresponding to emitter locations 1008 of the active marker device 1001.

Figure 10D:
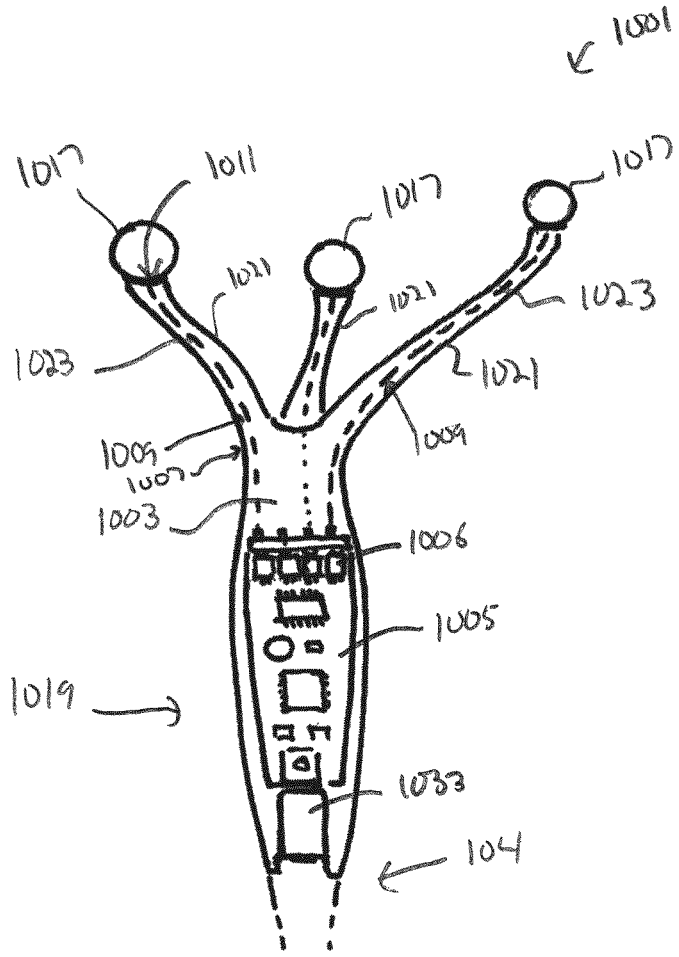

FIG. 10D illustrate an additional embodiment of an active marker device 1001 in which the electronics module 1005 is housed within the handle 1019 of a surgical tool 104. A rigid frame 1003 as described above may comprise a part or all of the handle 1019. The rigid frame 1003 includes a plurality of arms 1021 that extend from the handle 1019 of the tool 104. Each arm 1021 includes a channel 1009 that extends along the length of the arm 1021 to an opening 1011 at the end of the arm 1021. The optical guide apparatus 1007 includes a plurality of optical fibers 1023 that are located within respective channels 1009 of the frame 1003. The ends of the optical fibers 1023 may be positioned so that light is directed out of the respective openings 1011. The optical fibers 1023 direct light from at least one light source 1006 in the handle 1019 along the arms 1021 and out of the respective openings 1011. A plurality of diffusers 1017 may be located over the openings 1011.

The electronics module 1005 may be integrated with the rigid frame 1003 or may be removable from the frame 1003. FIG. 10D also illustrates a power source 1033 (e.g., battery) within the frame 1003 for providing power to the electronics module 1005. Alternatively, the electronics module 1005 may have an integrated power supply 1005. The rigid frame 1003 may be detachable from the rest of the surgical tool 104, or may be integral with the surgical tool 104.

In embodiments of an active marker device 1001 as described above, the optical guide apparatus 1007 may optionally be removable from the rigid frame 1003 and the components may be separately sterilized for reuse or disposed. In embodiments in which the rigid frame 1003, optical guide apparatus 1007 and electronics module 1005 are comprised of separate components, each of these components may be individually removed and separately sterilized for reuse or disposed. In some embodiments, one or more of the rigid frame 1003, optical guide apparatus 1007 and electronics module 1005 may be a single-use disposable component.

A plurality of active marker devices 1001 may utilize an identical design for the rigid frame 1003, with the differentiation between markers provided by differences in the pulse patterns produced by the electronics module 1005. This may provide an economical marker device 1001 that may be optimized for ergonomics or other factors.

In some embodiments, the electronics component may include at least one first light source that emits light (e.g., IR light) that is detectable by the motion tracking system 105 for tracking purposes as described above, and at least one second light source that emits visible light. The visible light from the at least one second light source may be coupled into the optical guide apparatus 1007 to provide the user with visual feedback from the marker device 1001. The visual feedback may provide feedback on the operation of the marker device 1001 itself (e.g., an indication of the charge state of the battery, an indication of whether the marker device is on, programmed and actively emitting IR light, etc.). In some embodiments, the electronics module 1005 may receive feedback data from an external device (such as computer 113) and may control the at least one second light source to provide visual feedback to the user based on the received feedback data. The visual feedback may provide feedback regarding a surgical procedure. For example, the at least one second light source may flash light of a certain color (e.g., green) when the tool to which the marker device 1001 is attached is determined to be in the correct position (e.g., at a target location or along a pre-set trajectory within the patient) and may flash a different color (e.g., yellow) when the tool is in an incorrect position. In addition, the visual feedback may indicate whether or not a tool is currently being tracked by the motion tracking system 105. The at least one first (IR) light source and the at least one second (visible) light source may be multiplexed so that only one source is emitting at a time.

Alternatively or in addition, a cover 1031 of the active marker device 1001 (see FIG. 10B) may comprise a transparent material over at least a portion of the cover 1031 to enable the user to view visual feedback from the at least one second light source through the cover 1031.

Figures 11A, 11B:
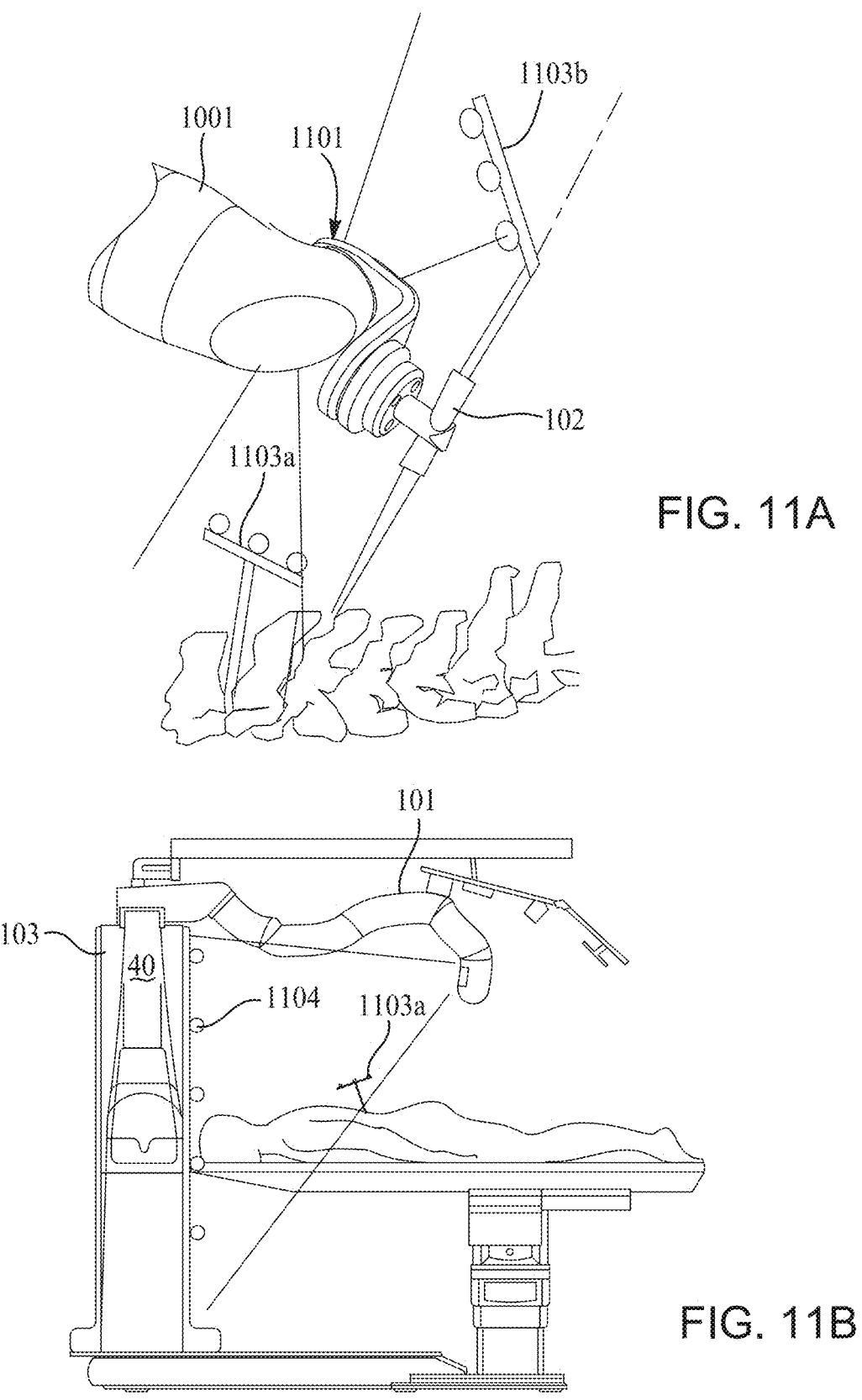
FIGS. 11A-11B illustrate a motion tracking system for robot-assisted imaged guided surgery that includes motion tracking sensors located on a robotic arm.

Further embodiments include a motion tracking system 105 for robotic-assisted image guided surgery that utilize an "inside out" architecture in which the sensors for tracking the marker devices are located on a robotic arm 101. An exemplary embodiment is illustrated in FIGS. 11A and 11B. In this embodiment, the robotic arm 101 includes a sensor array 1101 extending around the circumference of the arm 101 proximate to the end effector 102. The sensor array 1101 may include a plurality of outward-facing cameras, which may be similar to the cameras 107 described above with reference to FIGS. 1 and 2. The sensor array 1101 may also include one or more IR light sources for illuminating reflective marker. The sensor array 1101 may be configured to detect radiation from passive or active marker devices 1103 within the field of view of the sensor array 1101, which may be used to track the positions of the marker devices 1103 relative to the sensor array 1101 (e.g., using triangulation techniques) as described above. The position of the sensor array 1101 and of the end effector 102 within a common reference frame may be determined based on the robot joint coordinates and the known geometry of the robotic arm 101.

As shown in FIG. 11A, the sensor array 1101 may simultaneously track multiple marker devices 1103, including a first marker device 1103a attached to the patient and a second marker device 1103b attached to a tool 104 that is inserted in the end effector 102 of the robotic arm 101. The field of view of the sensor array 1101 may extend around the entire circumference of the robotic arm 101, and may encompass the entire surgical area. In embodiments, a separate marker device on the robotic arm 101 may not be necessary. Further, the need for an external optical sensing device, such as sensing device 111 shown in FIGS. 1 and 2, may be avoided.

In some embodiments, the sensor array 1103 may also be used for collision avoidance for the robotic arm 101. Optionally, the sensor array 1103 may include a user interface component, such as a touchscreen display interface, for controlling various operations of the robotic arm 101 and/or the image guided surgery system.

FIG. 11B illustrates the robotic arm 101 moved to a second position during an imaging scan using the imaging device 103. In this position, the sensor array 1103 has a clear view of both the patient marker device 1103a and additional markers 1104 on the imaging gantry 40, which may facilitate registration of image scan data, as discussed above in FIG. 3. The control system for the robotic arm 101 may be configured to move the robotic arm 101 to optimally position the sensor array 1103 for scan data registration during an imaging scan.

Figure 12:
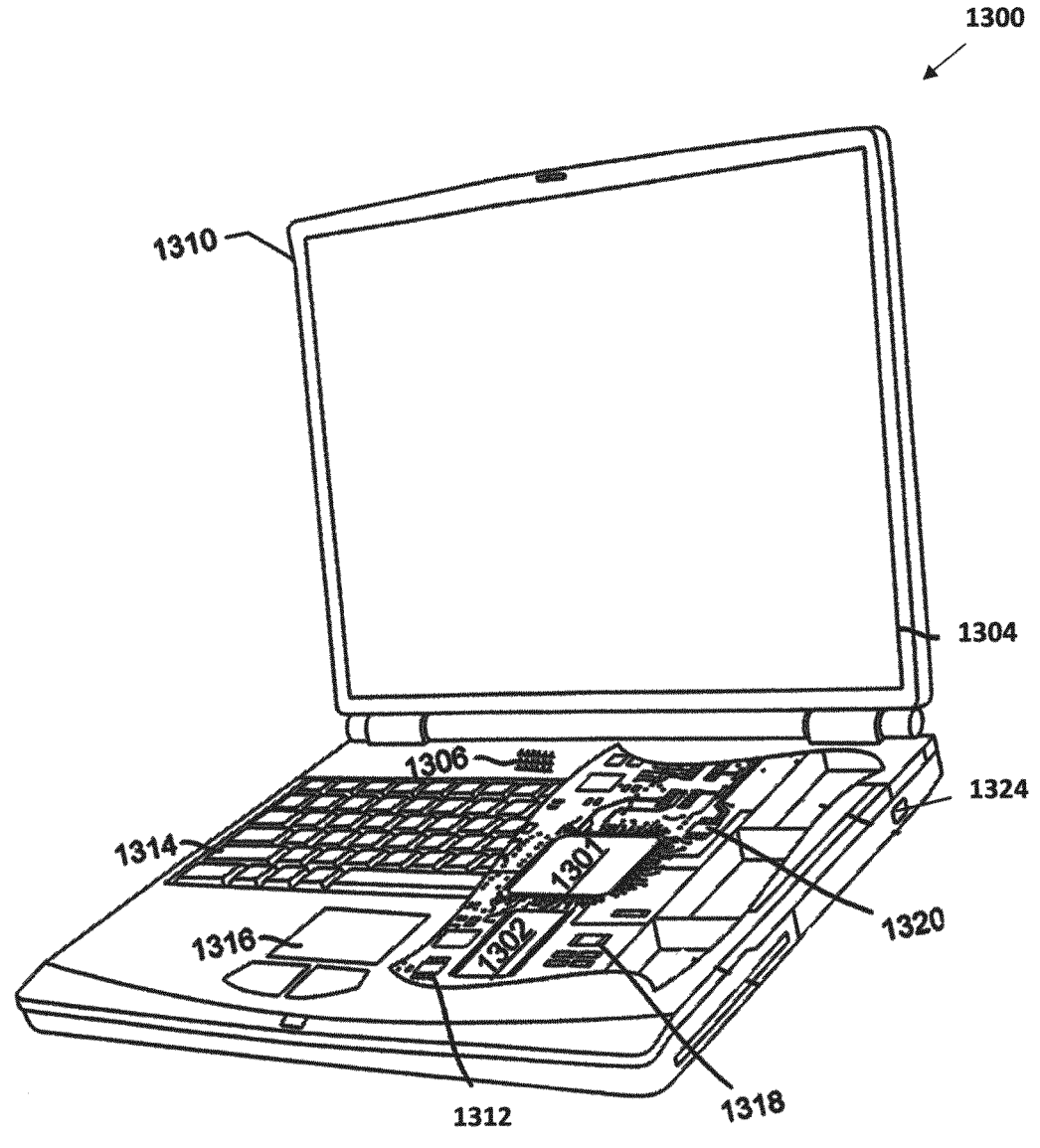
FIG. 12 schematically illustrates a computing device which may be used for performing various embodiments.

FIG. 12 is a system block diagram of a computing device 1300 useful for performing and implementing the various embodiments described above. The computing device 1300 may perform the functions of an image guided surgery system 400 and/or a robotic control system 405, for example. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a non-volatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A marker device for an image guided surgery system, comprising:
an electronics unit comprising at least one light source;
a rigid frame attached to a robotic arm of a surgical robot and to the electronics unit, the rigid frame having at least one channel extending from the electronics unit to at least one opening in the rigid frame, wherein the electronics unit is removable from the rigid frame; and
an optical guide apparatus located within the at least one channel to couple light from the at least one light source of the electronics unit to the at least one opening in the rigid frame, wherein the optical guide apparatus is removable from the rigid frame,
wherein the optical guide apparatus includes at least one optical fiber.

2. The marker device of claim 1, wherein the at least one optical fiber is a light pipe.

3. The marker device of claim 1, wherein the rigid frame comprises a plurality of channels extending from the electronics unit to a plurality of openings in the rigid frame, and the optical guide apparatus couples light from the at least one light source to each of the plurality of openings in the rigid frame.

4. The marker device of claim 1, wherein the electronics unit and the optical guide apparatus comprise an integral unit that is removable from the rigid frame.

5. The marker device of claim 1, wherein the electronics unit and the optical guide apparatus comprise separate components that are each removable from the rigid frame.

6. The marker device of claim 1, wherein the rigid frame is a re-sterilizable component configured for multiple surgical uses and at least one of the electronics unit and the optical guide apparatus comprises a single-use disposable component.

7. The marker device of claim 1, further comprising a plurality of optical diffusers located over the plurality of openings in the rigid frame.

8. The marker device of claim 1, further comprising an end effector attached to a distal end of the robotic arm, and wherein the rigid frame is attached to the end effector.

9. The marker device of claim 1, wherein the at least one light source comprises a light emitting diode (LED).

10. The marker device of claim 9, wherein the electronics unit comprises circuitry configured to control operation of the at least one light source; and
a communication circuit configured to communicate with an external device.

11. The marker device of claim 1, wherein the at least one light source comprises at least one infrared light source.

12. The marker device of claim 11, wherein the electronics unit further comprises at least one visible light source that is configured to provide visual feedback to a user.

13. The marker device of claim 12, wherein the optical guide apparatus couples light from the at least one visible light source to the at least one opening in the rigid frame.

14. A surgical system comprising:
a robotic arm including a plurality of links between a proximal end and a distal end of the robotic arm, each of the plurality of links having a respective outer surface with an opening extending through the outer surface;
an end effector attached to the distal end of the robotic arm; and a marker system for tracking the robotic arm using a
   motion tracking system, the marker system comprising:
     one or more marker devices having a frame attached to
       the end effector, at least one light source removably
       attached to the frame, and an optical guide located
       within and removable from the frame, the optical
       guide configured to transmit light from the light
       source through one or more channels in the frame,
       the optical guide comprising an optical fiber.

15. The system of claim 14, further comprising an imaging device, the imaging device including one or more markers, wherein the marker system is further configured for tracking the imaging device.

16. The system of claim 14, wherein the one or more marker devices comprise one or more active markers.

17. The system of claim 14, wherein the at least one light source comprises at least one infrared light source.

* * * * *